(12) United States Patent
Reinerth et al.

(10) Patent No.: US 11,061,327 B2
(45) Date of Patent: Jul. 13, 2021

(54) POLYIMIDES

(71) Applicant: FUJIFILM ELECTRONIC MATERIALS U.S.A. INC., N. Kingstown, RI (US)

(72) Inventors: William A. Reinerth, Riverside, RI (US); Binod B. De, Attleboro, MA (US); Sanjay Malik, Attleboro, MA (US); Raj Sakamuri, Sharon, MA (US); Ognian N. Dimov, Warwick, RI (US); Ahmad A. Naiini, East Greenwich, RI (US)

(73) Assignee: Fujifilm Electronic Materials U.S.A., Inc., N. Kingstown, RI (US)

( * ) Notice: Subject to any disclaimer, the term of this patent is extended or adjusted under 35 U.S.C. 154(b) by 127 days.

(21) Appl. No.: 16/084,306

(22) PCT Filed: Oct. 25, 2017

(86) PCT No.: PCT/US2017/058221
§ 371 (c)(1),
(2) Date: Sep. 12, 2018

(87) PCT Pub. No.: WO2018/085087
PCT Pub. Date: May 11, 2018

(65) Prior Publication Data
US 2019/0129303 A1    May 2, 2019

Related U.S. Application Data

(60) Provisional application No. 62/415,550, filed on Nov. 1, 2016.

(51) Int. Cl.
| | |
|---|---|
| *G03F 7/038* | (2006.01) |
| *H01L 23/29* | (2006.01) |
| *C08L 79/08* | (2006.01) |
| *C08G 73/14* | (2006.01) |
| *C08G 73/10* | (2006.01) |
| *C09D 179/08* | (2006.01) |

(Continued)

(52) U.S. Cl.
CPC .......... *G03F 7/0387* (2013.01); *C07C 211/50* (2013.01); *C08G 73/1078* (2013.01); *C08G 73/14* (2013.01); *C08L 79/08* (2013.01); *C09D 179/08* (2013.01); *G03F 7/162* (2013.01); *G03F 7/168* (2013.01); *G03F 7/2002* (2013.01); *G03F 7/325* (2013.01); *G03F 7/38* (2013.01); *G03F 7/40* (2013.01); *H01L 23/293* (2013.01)

(58) Field of Classification Search
CPC .............. G03F 7/0387; C08G 73/1078; C08G 73/1085
See application file for complete search history.

(56) References Cited

U.S. PATENT DOCUMENTS

| | | |
|---|---|---|
| 4,426,657 A | 1/1984 | Abiru et al. |
| 7,556,860 B2 | 7/2009 | Akiyama et al. |

(Continued)

FOREIGN PATENT DOCUMENTS

| | | | |
|---|---|---|---|
| WO | WO 2015/190645 | 12/2015 | .............. C08G 73/10 |
| WO | WO-2015190645 A1 * | 12/2015 | ................ C08J 5/18 |

OTHER PUBLICATIONS

English translation of WO2015190645. (Year: 2015).*

(Continued)

*Primary Examiner* — Chanceity N Robinson
*Assistant Examiner* — Anna Malloy
(74) *Attorney, Agent, or Firm* — Fish & Richardson P.C.

(57) ABSTRACT

A polyimide polymer that includes the reaction product of: (a) at least one diamine selected from the group consisting of a diamine of Structure (Ia) and a diamine of Structure (Ib),

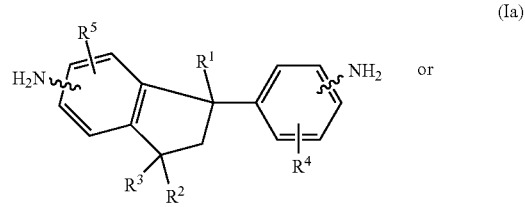

(Ia)

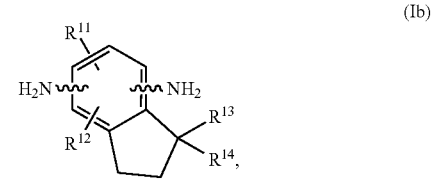

(Ib)

(b) at least one diamine of Structure (II),

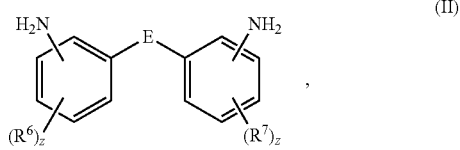

(II)

(c) at least one tetracarboxylic acid dianhydride, and optionally (d) at least one compound containing a first functional group reactive with an amine or an anhydride and at least one second functional group selected from the group consisting of a substituted or unsubstituted alkenyl group and a substituted or unsubstituted alkynyl group. Each variable in the above formulas is defined in the specification.

37 Claims, No Drawings

(51) Int. Cl.
*G03F 7/16* (2006.01)
*G03F 7/20* (2006.01)
*G03F 7/32* (2006.01)
*G03F 7/38* (2006.01)
*G03F 7/40* (2006.01)
*C07C 211/50* (2006.01)

(56) References Cited

U.S. PATENT DOCUMENTS

| 7,718,234 | B2* | 5/2010 | Tomioka | G02F 1/134363 |
| | | | | 428/1.2 |
| 9,695,284 | B2* | 7/2017 | Malik | C07C 211/09 |
| 10,604,628 | B2* | 3/2020 | Malik | C09D 179/08 |
| 2014/0343199 | A1* | 11/2014 | Malik | C09D 179/08 |
| | | | | 524/109 |
| 2015/0219990 | A1* | 8/2015 | Malik | G03F 7/38 |
| | | | | 428/473.5 |
| 2016/0313642 | A1 | 10/2016 | Malik et al. | |
| 2018/0311622 | A1* | 11/2018 | Sawada | B01D 69/02 |

OTHER PUBLICATIONS

Khune, Gajendra, "The Thermal and Electrical Behavior of Polyimide Films", Jan. 1981, Journal of Macromolecular Science: Part A—Chemistry, vol. 15 (2), 241-265. (Year: 1981).*
The International Preliminary Report on Patentability for International Application No. PCT/US2017/058221 dated May 16, 2019.
The International Search Report and Written Opinion of the International Searching Authority for International Application No. PCT/US2017/058221 dated Mar. 22, 2018 (12 pages).
PUBCHEM. Compound Summary for SID 135824948, Available Date: Jun. 13, 2012 (Retrieved on Nov. 21, 2017). Retrieved from the Internet: URL: https//pubchem.ncbi..nlm.nih.gov/substance/135824948 (7 pages).

* cited by examiner

POLYIMIDES

CROSS-REFERENCE TO RELATED APPLICATIONS

The present application is a U.S. National Phase application under 35 U.S.C. § 371 of International Patent Application No. PCT/US2017/058221, filed Oct. 25, 2017, which claims priority to U.S. Provisional Application Ser. No. 62/415,550, filed on Nov. 1, 2016, both of which are hereby incorporated by reference in their entirety.

BACKGROUND OF THE DISCLOSURE

The continued expansion of mobile computing applications requires the packing of ever growing levels of computing power in smaller device footprints. Designers of semiconductor devices are relying on the use of a variety of new chip architectures to meet the new device requirements. These new architectures include flip chip wafer bumping using copper pillars as well as approaches employing through silicon vias (TSV) such as three-dimensional integrated circuits (3D IC) in which wafers are thinned, the resulting dies are stacked and then connected by TSV and 2.5D interposer designs. These approaches pose significant challenges not only for the designers of these new IC architectures, but for the designers of the packaging materials that will be used for these devices.

Material requirements for packaging applications are continuously evolving as these new, advanced devices are relying heavily on wafer level packaging (WLP) and 3D integration. While there are a number of traditional packaging materials that have been employed through the years, polyimides, due to their excellent electrical, mechanical and thermal properties, have been the material of choice for semiconductor packaging applications. However, drawbacks of conventional polyimides include high cure temperatures (>350° C.), high post-cure shrinkage and high levels of moisture absorption. This high shrinkage leads to cured polyimide films having high residual stress which leads to bowing of the silicon wafer. The next generation chip architectures employing 3D integration require that the silicon wafers be thinned down up to 20 µm in most advanced applications in order to satisfy requirements for vertical integration. These thinned wafers are extremely fragile and excessive residual stress in the packaging material used will be catastrophic. The next generation packaging materials must be designed so as to impart minimal stress on the wafer. For this reason, low cure temperature and low post-cure shrinkage are among the critical requirements for advanced packaging materials.

Other traditional packaging materials, such as epoxies and BCB, can be cured at lower temperatures (<250° C.) and have lower residual stress than polyimides. Unfortunately, these materials suffer from their own limitations such as poor mechanical properties including a high coefficient of thermal expansion (CTE). Semiconductor substrates such as metals (aluminum, copper) and $SiO_2$ have low CTE. A packaging material with a high CTE creates a large thermal mismatch with the underlying substrate, which can lead to warpage and delamination of the packaging material.

Other limitations of conventional packaging materials include poor solubility and/or processability. Some packaging materials which have low residual stress and low CTE are only soluble in polar, aprotic solvents (NMP, DMAc) that are not acceptable to semiconductor manufacturers. Of those packaging materials that are soluble in acceptable solvents, most are not able to be coated using flexible application methods such as inkjet technology.

The demands being placed on advanced packaging materials are stringent. Presently, there exists no single material that satisfies all of the design requirements of next generation WLP applications. Table 1 shows the performance targets for next generation packaging materials and where each class of traditional packaging materials fails to meet the requirements.

TABLE 1

| | | Material platform | | | |
|---|---|---|---|---|---|
| Performance Targets | | Conventional | | | |
| Criteria | Target | PI/PBO | Epoxy | BCB | Siloxane |
| Cure Temperature | <170° C. | X | P | P | M |
| Low Stress | <20 MPa | X | M | M | M |
| CTE | <60 ppm/° C. | M | P | P | X |
| Film Shrinkage | <5% | X | M | M | M |
| Soluble in Semiconductor Friendly Solvents | No NMP | P | M | M | M |
| Resolution | <5 microns | M | M | P | M |
| Tensile Elongation at Break | >20% | M | P | X | X |
| Water Uptake | <0.5% | P | M | M | M |
| Ink Jet Capability | Yes | P | X | X | X |

X: Does not meet target
P: Partially meets target
M: Meets target

BRIEF SUMMARY OF THE DISCLOSURE

One objective of this disclosure is to provide novel polymers, polymeric compositions and processes employing them that will meet requirements for advanced packaging applications. In some embodiments, this disclosure features a polyimide polymer containing the reaction product of components (a), (b), (c), and optionally (d), in which (a), (b), (c), and (d) are:

(a) at least one diamine selected from the group consisting of a diamine of Structure (Ia) and a diamine of Structure (Ib):

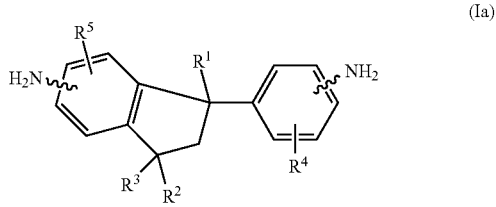

(Ia)

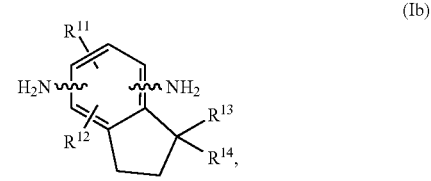

(Ib)

(b) at least one diamine of Structure (II):

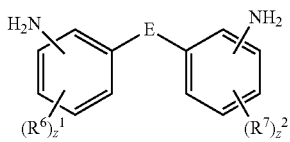

(c) at least one tetracarboxylic acid dianhydride, and optionally,
(d) at least one compound containing a first functional group reactive with an amine or an anhydride and at least one second functional group selected from the group consisting of a substituted or unsubstituted alkenyl group and a substituted or unsubstituted alkynyl group. In Structures (Ia), (Ib), and (II), each of $R^1$, $R^2$, $R^3$, $R^4$, $R^5$, $R^{11}$, $R^{12}$, $R^{13}$, and $R^{14}$, independently, is H, a substituted or unsubstituted $C_1$-$C_6$ linear or branched alkyl group, or a substituted or unsubstituted $C_5$-$C_8$ cycloalkyl group; each $R^6$ and each $R^7$, independently, is a hydrogen atom, a substituted or unsubstituted linear or branched $C_1$-$C_4$ alkyl group, a substituted or unsubstituted $C_5$-$C_8$ cycloalkyl group or a halogen atom; E is a $C_2$-$C_{40}$ substituted or unsubstituted unsaturated hydrocarbon provided that the two aminophenyl groups in Structure (II) are separated by no more than about 4 carbons and each of $z^1$ and $z^2$, independently, is an integer from 0 to 4.

In some embodiments, this disclosure features a polyamic acid polymer from the reaction product of components (a), (b), (c), and optionally (d) wherein components (a), (b), (c), and (d) are:
(a) at least one diamine selected from the group consisting of a diamine of Structure (Ia) and a diamine of Structure (Ib),

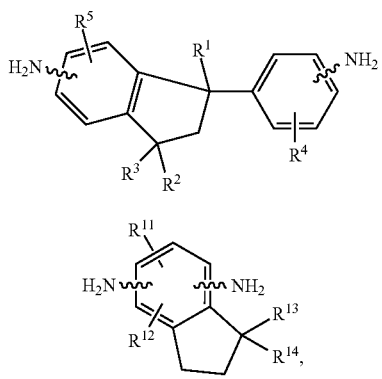

(b) at least one diamine of Structure (II)

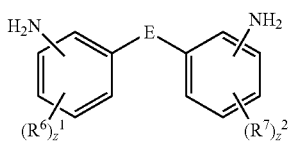

(c) at least one tetracarboxylic acid dianhydride, and optionally, (d) at least one compound containing a first functional group reactive with an amine or an anhydride and at least one second functional group selected from the group consisting of a substituted or unsubstituted alkenyl group and a substituted or unsubstituted alkynyl group. In Structures (Ia), (Ib), and (II), each of $R^1$, $R^2$, $R^3$, $R^4$, $R^5$, $R^{11}$, $R^{12}$, $R^{13}$, and $R^{14}$, independently, is H, a substituted or unsubstituted $C_1$-$C_6$ linear or branched alkyl group, or a substituted or unsubstituted $C_5$-$C_8$ cycloalkyl group, each $R^6$ and $R^7$ independently is a hydrogen atom, a substituted or unsubstituted linear or branched $C_1$-$C_4$ alkyl group, a substituted or unsubstituted $C_5$-$C_8$ cycloalkyl group or a halogen atom, E is a $C_2$-$C_{40}$ substituted or unsubstituted unsaturated hydrocarbon provided that the two aminophenyl groups are separated from each other by no more than about 4 carbons and each $z^1$ and $z^2$ independently is an integer from 0 to 4.

In some embodiments, this disclosure features a polyamic acid polymer from the reaction product of components (a), (b), (c), and optionally (d), in which components (a), (b), (c), and (d) are defined above.

In some embodiments, component (a) is at least one diamine of Structure (Ia). In such embodiments, the amino group on the indane ring in Structure (Ia) can be at the 5 position, the other amino group in Structure (Ia) can be at the 4 position. In some embodiments, each of $R^1$, $R^2$, and $R^3$ can be $CH_3$, and each of $R^4$ and $R^5$ can be H.

In some embodiments, the diamine of Structure (II) is a diamine of Structure (IIa):

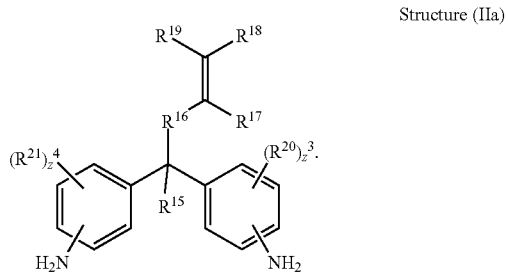

In Structure (IIa), each of $z^3$ and $z^4$, independently, is an integer ranging from 0 to 4; $R^{15}$ is a hydrogen atom, a substituted or unsubstituted linear or branched $C_1$-$C_4$ alkyl group, a substituted or unsubstituted $C_5$-$C_8$ cycloalkyl group, a substituted or unsubstituted phenyl group, or $-R^{22}-C(R^{23})=C(R^{24}R^{25})$, in which $R^{22}$ is $-(CH_2)_{z^6}-$; each of $R^{23}$, $R^{24}$ and $R^{25}$, independently, is a hydrogen atom, a substituted or unsubstituted linear or branched $C_1$-$C_4$ alkyl group, a substituted or unsubstituted $C_5$-$C_8$ cycloalkyl group, or a substituted or unsubstituted phenyl group; and $z^6$ is an integer from 0 to 4; $R^{16}$ is $-(CH_2)_{z^5}-$, in which $z^5$ is an integer from 0 to 4; each of $R^{17}$, $R^{18}$, and $R^{19}$, independently, is a hydrogen atom, a substituted or unsubstituted linear or branched $C_1$-$C_4$ alkyl group, a substituted or unsubstituted $C_5$-$C_8$ cycloalkyl group, a substituted or unsubstituted phenyl group; each $R^{20}$ and each $R^{21}$, independently, is a hydrogen atom, a substituted or unsubstituted linear or branched $C_1$-$C_4$ alkyl group, a substituted or unsubstituted $C_5$-$C_8$ cycloalkyl group or a halogen atom.

In some embodiments, the diamine of Structure (II) is a diamine of Structure (IIb):

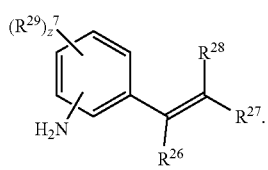

Structure (IIb)

In structure (IIb), each of $R^{26}$, $R^{27}$ and $R^{28}$, independently, is a hydrogen atom, a substituted or unsubstituted linear or branched $C_1$-$C_4$ alkyl group, a substituted or unsubstituted $C_5$-$C_8$ cycloalkyl group, a substituted or unsubstituted phenyl group, or a group represented by Structure (III):

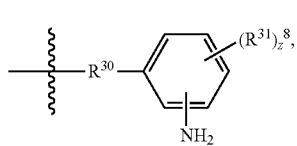

Structure (III)

in which $R^{30}$ is a single bond or a substituted or unsubstituted linear or branched $C_1$-$C_3$ alkylene; each $R^{31}$, independently, is a hydrogen atom, a substituted or unsubstituted linear or branched $C_1$-$C_4$ alkyl group, a substituted or unsubstituted $C_5$-$C_8$ cycloalkyl group or a halogen atom; and $Z^8$ is an integer from 0 to 4, with the proviso that at most one of $R^{26}$, $R^{27}$ or $R^{28}$ is a group represented by Structure (III). Further, in Structure (IIb), $R^{29}$ is a hydrogen atom, a substituted or unsubstituted linear or branched $C_1$-$C_4$ alkyl group, a substituted or unsubstituted $C_5$-$C_8$ cycloalkyl group or a halogen atom; and $z^7$ is an integer from 0 to 4.

In some embodiments, the first functional group reactive to an amine in component (d) can include an anhydride group, an acid halide group, an epoxy group, or an isocyanate group. In some embodiments, the first functional group reactive to an anhydride in component (d) can include an amino group, a hydroxyl group, or a thiol group.

In some embodiments, the molar ratio of components (a) and (b) to component (c) can range from 1.01 to 1.4 or from 0.8 to 0.99.

In some embodiments, this disclosure features a composition containing (A) at least one polyimide polymer described herein; (B) at least one reactive functional compound (RFC) having at least one functional group capable of reacting with a substituted or unsubstituted alkenyl group or a substituted or unsubstituted alkynyl group on the polyimide polymer; (C) an initiator capable of initiating a reaction between a substituted or unsubstituted alkenyl group or a substituted or unsubstituted alkynyl group on the polyimide polymer and the RFC; and (D) at least one solvent.

In some embodiments, component (B) (i.e., the reactive functional compound) can include a vinyl group, an allyl group, a vinyl ether group, a propenyl ether group, a (meth)acryloyl group, an epoxy group, a SiH group, or a thiol group.

In some embodiments, the composition includes other additives including, but are not limited to, adhesion promoters, plasticizers, surfactants, dyes, particles, etc.

In some embodiments, this disclosure features a process that includes coating a substrate with a composition described herein (e.g., a polyimide composition) to form a coated substrate having a film on the substrate, and baking the coated substrate to form a coated substrate having a dried film. In such embodiments, the coated substrate can be baked at a temperature from about 50° C. to about 200° C. The process can further includes one or more of the following steps: (1) exposing the dried film to radiation through a mask to form a coated substrate having a dried, patternwise exposed film, (2) baking the dried, patternwise exposed film at a temperature from about 50° C. to about 150° C. in a second baking step, (3) developing a portion of the dried, exposed film in a developer to produce a relief image on the substrate, and (4) rinsing the relief image on the substrate with a solvent or a mixture of solvents.

In some embodiments, this disclosure features a dry film structure that includes a carrier substrate, a protective layer, and a polymeric layer between the carrier substrate and the protective layer. The polymeric layer contains a polyimide composition containing components (A), (B), and (C) described above.

In some embodiments, this disclosure features a process that includes (a) removing the protective layer from the dry film structure described above, and (b) applying the film structure obtained in step (a) onto an electronic substrate to form a laminate, in which the polymeric layer is between the electronic substrate and the carrier substrate. The process can further include one or more of the following steps: (1) exposing the polymeric layer in the laminate to actinic radiation, (2) removing the carrier substrate before or after exposing the polymeric layer, (3) removing unexposed portions in the polymeric layer by using a developer and (4) curing the remaining polymeric layer.

In some embodiments, this disclosure features a process that includes (a) providing a dry film structure containing a carrier substrate, a protective layer, and a polymeric layer between the carrier substrate and the protective layer, in which the first polymeric layer includes at least one polyimide polymer of this disclosure, at least one reactive functional compound, and at least one initiator; (b) removing the protective layer from the dry film structure; (c) applying the structure obtained in step (b) onto an electronic substrate to form a laminate, the laminate containing the first polymeric layer between the electronic substrate and the carrier substrate; and (d) converting the polymeric layer into a patterned layer.

In some embodiments, this disclosure features an article formed by a process described herein. Examples of such articles include a semiconductor substrate, a flexible film for electronics, a wire isolation, a wire coating, a wire enamel, or an inked substrate. In some embodiments, this disclosure features a semiconductor device containing the article described above. For example, the semiconductor device can be an integrated circuit, a light emitting diode, a solar cell, and a transistor.

In some embodiments, this disclosure features a compound of Structure (IIa):

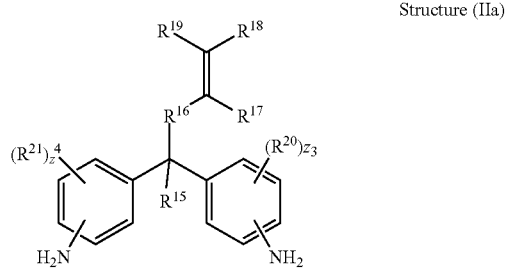

Structure (IIa)

in which each of $z^3$ and $z^4$, independently, is an integer from 0 to 4; $R^{15}$ is a hydrogen atom, a substituted or unsubstituted linear or branched $C_1$-$C_4$ alkyl group, a substituted or unsubstituted $C_5$-$C_8$ cycloalkyl group, a substituted or unsubstituted phenyl group, or —$R^{22}$—$C(R^{23})$=$C(R^{24}R^{25})$ in which $R^{22}$ is —$(CH_2)_z{}^6$—, each of $R^{23}$, $R^{24}$ and $R^{25}$, independently, is a hydrogen atom, a substituted or unsubstituted linear or branched $C_1$-$C_4$ alkyl group, a substituted or unsubstituted $C_5$-$C_8$ cycloalkyl group, or a substituted or unsubstituted phenyl group, and $z^6$ is an integer from 0 to 4; $R^{16}$ is —$(CH_2)_z{}^5$—, in which $z^5$ is an integer from 0 to 4; each of $R^{17}$, $R^{18}$, and $R^{19}$, independently, is a hydrogen atom, a substituted or unsubstituted linear or branched $C_1$-$C_4$ alkyl group, a substituted or unsubstituted $C_5$-$C_8$ cycloalkyl group, a substituted or unsubstituted phenyl group; and each $R^{20}$ and each $R^{21}$, independently, is a hydrogen atom, a substituted or unsubstituted linear or branched $C_1$-$C_4$ alkyl group, a substituted or unsubstituted $C_5$-$C_8$ cycloalkyl group or a halogen atom.

In some embodiments, a subset of the compounds of Structure (II) are those in which $z^3$ and $z^4$ are 0. In such embodiments $R^{15}$ can be $CH_3$, $R^{16}$ can be —$(CH_2)$—, and each of $R^{17}$, $R^{18}$, and $R^{19}$ can be H.

DETAILED DESCRIPTION OF THE DISCLOSURE

Definition of Terms

In the context of this disclosure, the term "tetravalent group" used in relation to polyimide polymers or monomers used to synthesize the polyimide polymers refers to a group containing four bonds (tetravalent), which can function as part of the polymer backbone or will become part of an imide group after processing. Other substituents, if allowed, can be present but are not of the type that will be integrated into the backbone or the imide group. The term "divalent group" refers to a group that is linked to two designated moieties. Any allowed substituents on the divalent group are not of the same type as the designated moieties.

In this disclosure, the term "reaction product" refers to a product formed from one or more synthetic steps. In general, the reactions that can be used to form a polyimide polymer described herein as a reaction product can include at least condensation and imidization reactions, and optionally endcapping reactions. In some embodiments, a polyimide reaction product can be formed by reacting diamines and dianhydrides described herein through condensation, imidization and endcapping reactions in this order. In some embodiments, a polyimide reaction product can be formed by reacting diamines and dianhydrides described herein through condensation, endcapping and imidization reactions in this order. In some embodiments, the condensation and endcapping reactions can be performed in one step, followed by imidization. In other embodiments, the condensation and endcapping reactions can be performed in two steps, followed by imidization. In general, the reactions that can be used to form a polyamic acid polymer described herein as a reaction product can include at least condensation reactions, and optionally endcapping reactions.

The term "alkyl" refers to a saturated, linear or branched hydrocarbon group, such as —$CH_3$ or —$CH(CH_3)_2$. The term "alkylene" refers to a saturated, linear or branched hydrocarbon divalent group, such as —$(CH_2)_2$—. The term "alkenyl" refers to a linear or branched hydrocarbon group that contains at least one double bond, such as —CH=CH—$CH_3$. The term "alkynyl" refers to a linear or branched hydrocarbon group that contains at least one triple bond, such as —C≡C—$CH_3$. The term "cycloalkyl" refers to a saturated, cyclic hydrocarbon group, such as cyclohexyl. The term "aryl" refers to a hydrocarbon group having one or more aromatic rings. Examples of aryl groups include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl groups include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "aliphatic group" refers to a non-aromatic, saturated or unsaturated hydrocarbon group that can be linear, branched, cyclic, or polycyclic. An aliphatic group that optionally contains one or more oxygen, sulfur, or nitrogen atoms, or a mixture thereof refers to a saturated or unsaturated hydrocarbon group that optionally contains one or more oxygen, sulfur, or nitrogen atoms, or a mixture thereof. Examples of aliphatic groups include alkyl, alkenyl, alkynyl, and cycloalkyl groups.

Substituents on alkyl, alkenyl, alkynyl, cycloalkyl, aryl, and heteroaryl groups include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, amidino, guanidine, ureido, cyano, nitro, nitroso, azido, acyl, carbamate, thioacyl, acyloxy, carboxyl, and carboxylic ester.

The terms "one or more" and "at least one" are used interchangeably. The terms "films" and "coatings" can be used interchangeably.

The terms "moieties" and "groups" are used interchangeably. Likewise their singulars are used interchangeably.

The term "tacky" is used to describe a film that has been formed on a substrate that still has substantial solvent content but is no longer pourable or highly flowable.

Polyimide Polymers

One embodiment of this disclosure concerns a polyimide polymer containing the reaction product of components (a), (b), (c), and optionally (d), in which components (a), (b), (c), and (d) are:

(a) at least one diamine selected from the group consisting of a diamine of Structure (Ia) and a diamine of Structure (Ib):

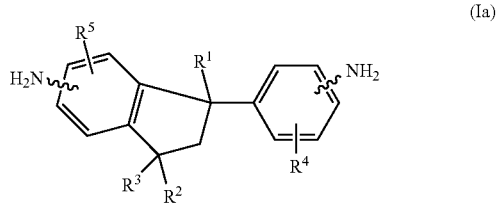

-continued

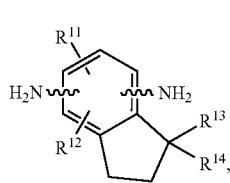
(Ib)

(b) at least one diamine of Structure (II):

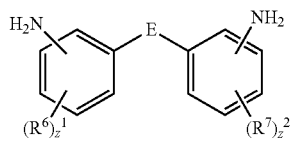
Structure (II)

(c) at least one tetracarboxylic acid dianhydride, and optionally,
(d) at least one compound containing a first functional group reactive with an amine or an anhydride and at least one second functional group selected from the group consisting of a substituted or unsubstituted alkenyl group and a substituted or unsubstituted alkynyl group. In Structures (Ia), (Ib), and (II), each of $R^1$, $R^2$, $R^3$, $R^4$, $R^5$, $R^{11}$, $R^{12}$, $R^{13}$, and $R^{14}$, independently, is H, a substituted or unsubstituted $C_1$-$C_6$ linear or branched alkyl group, or a substituted or unsubstituted $C_5$-$C_8$ cycloalkyl group; each $R^6$ and each $R^7$, independently, is a hydrogen atom, a substituted or unsubstituted linear or branched $C_1$-$C_4$ alkyl group, a substituted or unsubstituted $C_5$-$C_8$ cycloalkyl group or a halogen atom; E is a $C_2$-$C_{40}$ (e.g., $C_2$-$C_{30}$, $C_2$-$C_{25}$, $C_2$-$C_{20}$, $C_2$-$C_{15}$ or $C_2$-$C_{10}$) substituted or unsubstituted unsaturated hydrocarbon provided that the two aminophenyl groups in Structure (II) are separated from each other by no more than about 4 carbons (i.e., no more than 1, 2, 3, or 4 carbons) and each of $z^1$ and $z^2$, independently, is an integer from 0 to 4.

Examples of the substituted or unsubstituted $C_1$-$C_6$ linear or branched alkyl groups in $R^1$, $R^2$, $R^3$, $R^4$, $R^5$, $R^{11}$, $R^{12}$, $R^{13}$, and $R^{14}$ include, but are not limited to, methyl, ethyl, propyl, isopropyl, butyl, isobutyl, t-butyl, amyl, hexyl, and 2-methylhexyl. Examples of the $C_5$-$C_7$ cycloalkyl group in $R^1$, $R^2$, $R^3$, $R^4$, $R^5$, $R^{11}$, $R^{12}$, $R^{13}$, and $R^{14}$ include, but are not limited to, cyclopentyl, cyclohexyl, and cycloheptyl.

Specific examples of diamines of Structure (Ia) or (Ib) include, but are not limited to, 1-(4-aminophenyl)-1,3,3-trimethylindan-5-amine (alternative names including 4,4'-[1,4-phenylene-bis(1-methylethylidene)] bisaniline, 1-(4-aminophenyl)-1,3,3-trimethyl-2H-inden-5-amine, 1-(4-aminophenyl)-1,3,3-trimethyl-indan-5-amine, [1-(4-aminophenyl)-1,3,3-trimethyl-indan-5-yl]amine, and 1-(4-aminophenyl)-2,3-dihydro-1,3,3-trimethyl-1H-inden-5-amine), 5-amino-6-methyl-1-(3'-amino-4'-methylphenyl)-1,3,3-trimethylindan, 4-amino-6-methyl-1-(3'-amino-4'-methylphenyl)-1,3,3-trimethylindan, 5,7-diamino-1,1-dimethylindan, 4,7-diamino-1,1-dimethylindan, 5,7-diamino-1,1,4-trimethylindan, 5,7-diamino-1,1,6-trimethylindan, and 5,7-diamino-1,1-dimethyl-4-ethylindan.

In the diamine of Structure (II), E can be a $C_2$-$C_{40}$ (e.g. $C_2$-$C_{30}$, $C_2$-$C_{25}$, $C_2$-$C_{20}$, $C_2$-$C_{15}$ or $C_2$-$C_{10}$) substituted or unsubstituted unsaturated hydrocarbon provided that the two aminophenyl groups in Structure (II) are separated by no more than about 4 carbons. Examples of E include, but are not limited to, the following groups:

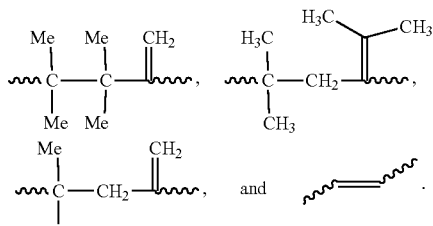

In some embodiments, the diamine of Structure (II) is a diamine of Structure (IIa):

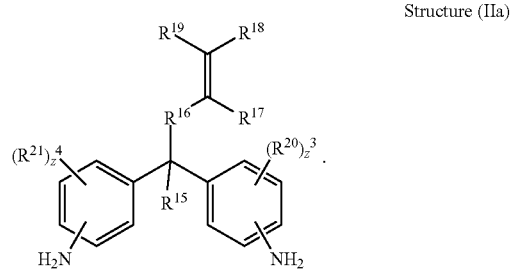
Structure (IIa)

In Structure (IIa), each of $z^3$ and $z^4$, independently, is an integer ranging from 0 to 4; $R^{15}$ is a hydrogen atom, a substituted or unsubstituted linear or branched $C_1$-$C_4$ alkyl group, a substituted or unsubstituted $C_5$-$C_8$ cycloalkyl group, a substituted or unsubstituted phenyl group, or —$R^{22}$—$C(R^{23})$=$C(R^{24}R^{25})$, in which $R^{22}$ is —$(CH_2)_z^6$—, each of $R^{23}$, $R^{24}$ and $R^{25}$, independently, is a hydrogen atom, a substituted or unsubstituted linear or branched $C_1$-$C_4$ alkyl group, a substituted or unsubstituted $C_5$-$C_8$ cycloalkyl group, or a substituted or unsubstituted phenyl group, and $z^6$ is an integer from 0 to 4; $R^{16}$ is —$(CH_2)_z^5$—, in which $z^5$ is an integer from 0 to 4; each of $R^{17}$, $R^{18}$, and $R^{19}$, independently, is a hydrogen atom, a substituted or unsubstituted linear or branched $C_1$-$C_4$ alkyl group, a substituted or unsubstituted $C_5$-$C_8$ cycloalkyl group, a substituted or unsubstituted phenyl group; each $R^{20}$ and each $R^{21}$, independently, is a hydrogen atom, a substituted or unsubstituted linear or branched $C_1$-$C_4$ alkyl group, a substituted or unsubstituted $C_5$-$C_8$ cycloalkyl group or a halogen atom.

Examples of $R^{15}$ in Structure (II) include, but are not limited to, Me, Et, n-Pr, i-Pr, n-Bu, cyclopentyl, cyclohexyl, propenyl, 1-methyl propenyl, 1-ethyl propenyl, and 1,1,2,-trimethyl propenyl. Examples of $R^{16}$ in Structure (II) include, but are not limited to, methylene, ethylene, n-propylene and n-butylene. Examples of $R^{17}$, $R^{18}$, and $R^{19}$ in Structure (II) include, but are not limited to, Me, Et, n-Pr, i-Pr, n-Bu, cyclopentyl, cyclohexyl, phenyl and tolyl. Examples of $R^{20}$ and $R^{21}$ in Structure (II) include, but are not limited to, Me, Et, i-Pr, n-Pr, n-Bu, cyclopentyl and cyclohexyl.

Examples of diamines of Structure (IIa) include, but are not limited to:

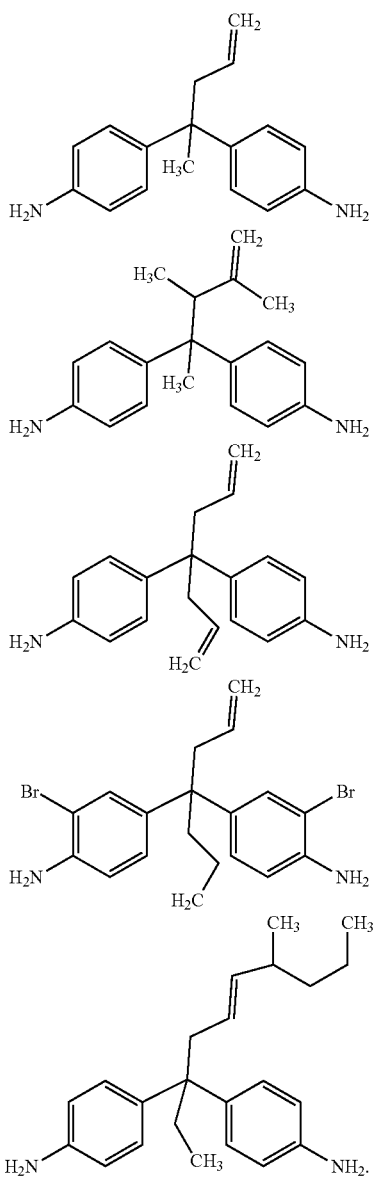

In some embodiments, the diamine of Structure (II) is a diamine of Structure (IIb):

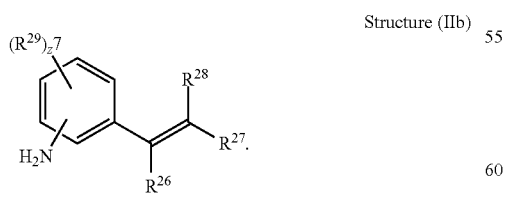

Structure (IIb)

In Structure (IIb), each of $R^{26}$, $R^{27}$ and $R^{28}$, independently, is a hydrogen atom, a substituted or unsubstituted linear or branched $C_1$-$C_4$ alkyl group, a substituted or unsubstituted $C_5$-$C_8$ cycloalkyl group, a substituted or unsubstituted phenyl group, or a group represented by Structure (III):

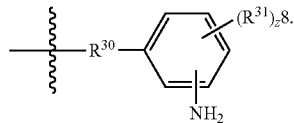

Structure (III)

In Structure (III), $R^{30}$ is a single bond or a substituted or unsubstituted linear or branched $C_1$-$C_3$ alkylene; and each $R^{31}$, independently, is a hydrogen atom, a substituted or unsubstituted linear or branched $C_1$-$C_4$ alkyl group, a substituted or unsubstituted $C_5$-$C_8$ cycloalkyl group or a halogen atom, $Z^8$ is an integer from 0 to 4 with the proviso that at most one of $R^{26}$, $R^{27}$ or $R^{28}$ is a group represented by Structure (III). Further, in Structure (IIb), $R^{29}$ is a hydrogen atom, a substituted or unsubstituted linear or branched $C_1$-$C_4$ alkyl group, a substituted or unsubstituted $C_5$-$C_8$ cycloalkyl group or a halogen atom; and $z^7$ is an integer from 0 to 4.

Examples of $R^{26}$, $R^{27}$, and $R^{28}$ in Structure (IIb) include, but are not limited to, Me, Et, n-Pr, i-Pr, n-Bu, cyclopentyl, cyclohexyl, phenyl, tolyl, and groups with the following structures:

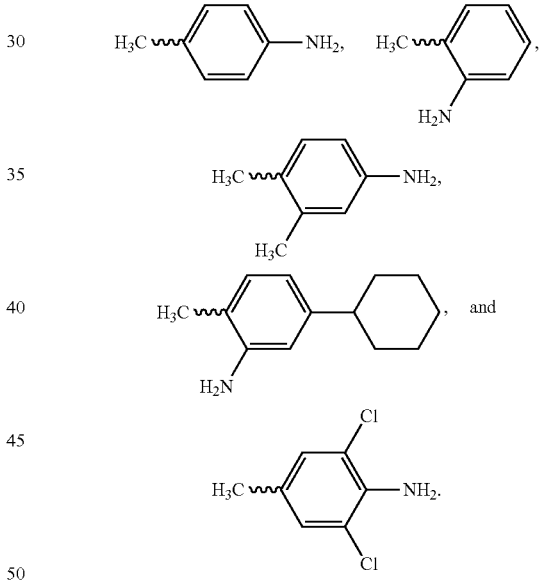

Examples of diamines of Structure (IIb) include, but are not limited to:

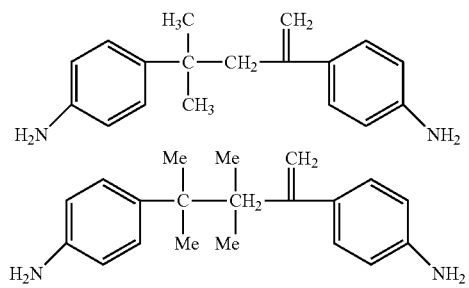

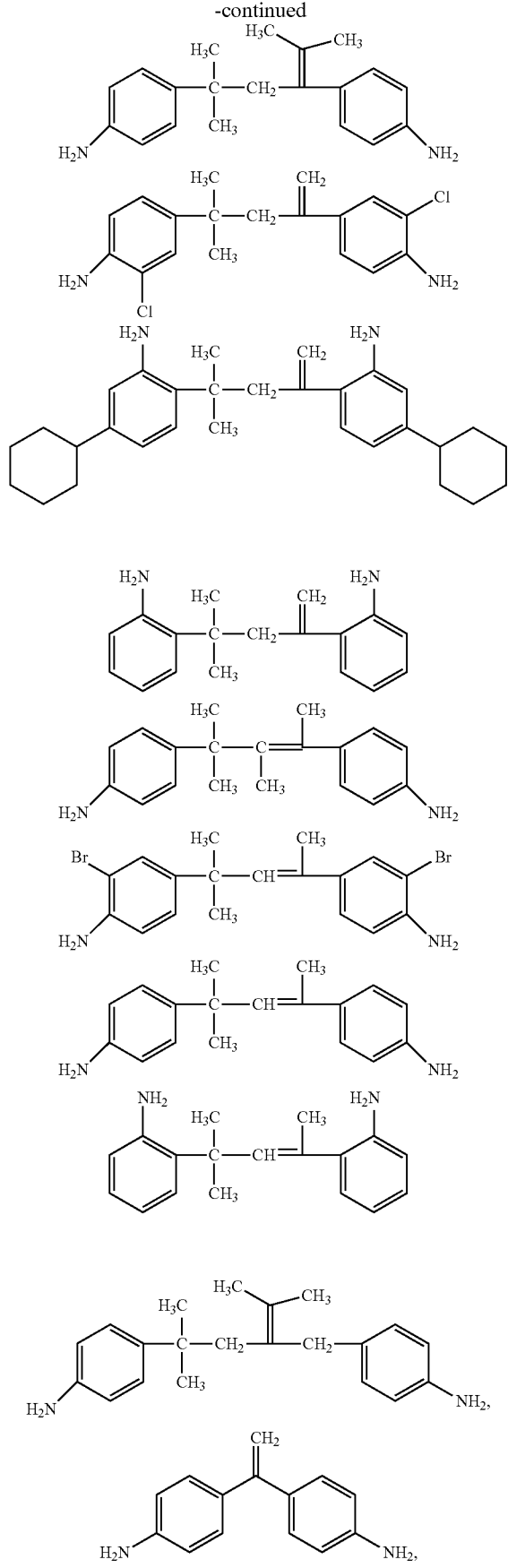

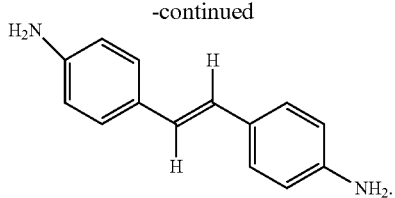

In some embodiments, the polyimides of this disclosure can also be made from diamines in addition to the diamines of Structure (Ia), (Ib), or (II) as long as the solubility of the resulting polyimide polymers in solvents (such as GBL and NMP) is 10 wt. % or higher. Examples of suitable additional diamines include, but are not limited to, p-phenylenediamine, m-phenylenediamine, o-phenylenediamine, 3-methyl-1,2-benzene-diamine, 1,5-diaminonaphthalene, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,2-diaminocyclohexane, 1,4-diaminocyclohexane, 1,3-cyclohexanebis(methylamine), 5-amino-1,3,3-trimethyl cyclohexanemethanamine, 2,5-diaminobenzotrifluoride, 3,5-diaminobenzotrifluoride, 1,3-diamino-2,4,5,6-tetrafluorobenzene, 4,4'-oxydianiline, 3,4'-oxydianiline, 3,3'-oxydianiline, 3,3'-diaminodiphenylsulfone, 4,4'-diaminodiphenylsulfones, 4,4'-isopropylidenedianiline, 4,4'-diaminodiphenylmethane, 2,2-bis(4-aminophenyl)propane, 4,4' diaminodiphenyl propane, 4,4'-diaminodiphenyl sulfide, 4,4'-diaminodiphenylsulfone, 4-aminophenyl-3-aminobenzoate, 2,2'-dimethyl-4,4'-diaminobiphenyl, 3,3'-dimethyl-4,4'-diaminobiphenyl, 2,2'-bis (trifluoromethyl) benzidine, 3,3'-bis (trifluoromethyl) benzidine, 2,2-bis [4-(4-aminophenoxy phenyl)] hexafluoropropane, 2,2-bis (3-amino-4-methylphenyl)-hexafluoropropane, 2,2-bis(3-aminophenyl)-1,1,1,3,3,3-hexafluoropropane, 1,3-bis-(4-aminophenoxy)benzene, 1,3-bis-(3-aminophenoxy)benzene, 1,4-bis-(4-aminophenoxy)benzene, 1,4-bis-(3-aminophenoxy)benzene, 1-(4-aminophenoxy)-3-(3-aminophenoxy)benzene, 2,2'-bis-(4-phenoxyaniline)isopropylidene, N,N-bis(4-aminophenyl) aniline, bis(p-beta-amino-t-butylphenyl)ether, p-bis-2-(2-methyl-4-aminopentyl)benzene, p-bis(1,1-dimethyl-5-aminopentyl)benzene, 3,3'-dimethyl-4,4'-diaminobiphenyl, 3,3'-dimethoxybenzidine, 4,4'-diaminobenzophenone, 3'-dichlorobenzidine, 2,2-bis [4-(4-aminophenoxy)phenyl] propane, 4,4'-[1,3-phenylenebis(1-Methyl-ethylidene)] bisaniline, 4,4'-[1,4-phenylenebis(1-methyl-ethylidene)] bisaniline, 2,2-bis [4-(4-aminophenoxy) phenyl] sulfone, 2,2-bis [4-(3-aminophenoxy) benzene], 1,4-bis (4-aminophenoxy) benzene, 1,3-bis (4-aminophenoxy) benzene, (1,3'-bis (3-aminophenoxy) benzene, 2,6-diamino-9H-thioxanthen-9-one, 2,6-diaminoanthracene-9,10-dione, and 9H-fluorene-2,6-diamine.

Examples of preferred additional diamines include, but are not limited to, m-phenylenediamine, 1,5-diaminonaphthalene, 2,5-diaminobenzotrifluoride, 3,5-diaminobenzotrifluoride, 4,4'-oxydianiline, 4,4'-diaminodiphenylsulfones, 2,2-bis(4-aminophenyl)propane, 4-aminophenyl-3-aminobenzoate, 2,2-bis [4-(4-aminophenoxy phenyl)] hexafluoropropane, 2,2-bis (3-amino-4-methylphenyl)-hexafluoropropane, 2,2-bis(3-aminophenyl)-1,1,1,3,3,3-hexafluoropropane, 1,3-bis-(4-aminophenoxy)benzene, 1,3-bis-(3-aminophenoxy)benzene, 1-(4-aminophenoxy)-3-(3-aminophenoxy)benzene, 2,2'-bis-(4-phenoxyaniline) isopropylidene, 3,3'-dimethyl-4,4'-diaminobiphenyl, 3,3'- dimethoxybenzidine, 4,4'-diaminobenzophenone, 2,2-bis [4-(4-aminophenoxy)phenyl] propane, 4,4'-[1,3-phenylenebis (1-Methyl-ethylidene)] bisaniline, 4,4'-[1,4-phenylenebis(1-methyl-ethylidene)]bisaniline, 2,2-bis [4-(4-aminophenoxy) phenyl] sulfone, 2,2-bis [4-(3-aminophenoxy) benzene], 1,3'-bis (3-aminophenoxy) benzene, 2,6-diamino-9H-thioxanthen-9-one, and 2,6-diaminoanthracene-9,10-dione.

In some embodiments, the molar percentage of the diamine of Structure (Ia) can be from 0% to 100% (e.g., from 5% to 95%, from 10% to 90%, from 20% to 80%, from 30% to 70%, from 40% to 60%, or 50%) of the total amount of the diamines of Structures (Ia) and (Ib).

In some embodiments, the molar percentage of the diamines of Structures (Ia) and (Ib) in the total amount of diamines is at least about 30% (e.g., at least about 35%, at least about 40%, at least about 45%, or at least about 50%) to at most about 95% (e.g., at most about 90%, at most about 85%, at most about 80%, at most about 75% or at most about 70%).

In some embodiments, the molar percentage of the diamines of Structure (II) in the total amount of diamines is at least about 5% (e.g., at least about 7.5%, at least about 10%, at least about 12.5%, or at least about 15%) to at most about 70% (e.g., at most about 60%, at most about 50%, at most about 40%, at most about 30% or at most about 20%).

In some embodiments, the total molar percentage of the diamines of Structures (Ia), (Ib), and (II) in the total amount of diamines used to prepare the polyimide polymer is from at least about 60% (e.g., at least about 65%, at least about 70%, or at least about 75%) to at most about 100% (e.g., at most about 95%, at most about 90%, or at most about 85%).

In some embodiments, the molar percentage of the diamines of Structures (Ia) and (Ib) in the total amount of diamines of Structures (Ia), (Ib), and (II) is at least about 60% (e.g., at least about 65%, at least about 70%, at least about 75%, or at least about 80%) to at most about 95% (e.g., at most about 90% or at most about 85%).

In some embodiments, the molar percentage of the diamines of Structure (II) in the total amount of diamines of Structure (Ia), (Ib), and (II) is at least about 2.5% (e.g., at least about 10%, or at least about 15%) to at most about 40% (e.g., at most about 35% or at most about 20%).

In general, to form a polyimide polymer described herein, the diamines of Structures (Ia) and/or Structures (Ib) and Structure (II) (and any additional optional diamines) can be reacted with at least one tetracarboxylic acid dianhydride. Preferred tetracarboxylic acid dianhydrides have the Structure (V) with a moiety Y.

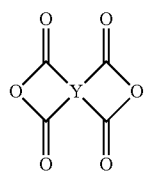

Structure (V)

The moiety Y is a tetravalent organic group selected from the group consisting of:
a) a substituted or unsubstituted $C_6$-$C_{18}$ aryl or heteroaryl group,
b) a substituted or unsubstituted $C_2$-$C_{18}$ linear, branched, cyclic or fused polycyclic alkylene group,
c) a substituted or unsubstituted heterocyclic group,
d) a tetravalent group of Structure (VI-a), (VI-b), (VI-c), (VI-d), (VI-e), (VI-f), (VI-g), (VI-h), (VI-i), or (VI-j), where $R^{32}$ to $R^{42}$ are independently a hydrogen atom or a substituted or unsubstituted $C_1$-$C_{10}$ linear or branched alkyl group (e.g., a partially or fully halogen substituted $C_1$-$C_{10}$ alkyl group) and $L^3$ to $L^6$ are independently selected from the group consisting of an unsubstituted or substituted carbon atom, an oxygen atom, a sulfur atom, a —(C=O)— group, a —[S(=O)$_2$]— group and a —(S=O)— group,

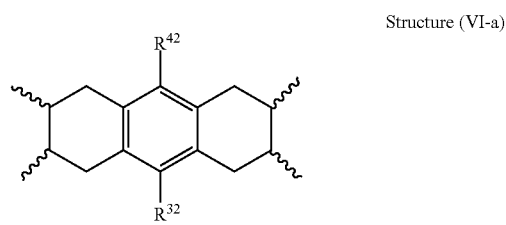

Structure (VI-a)

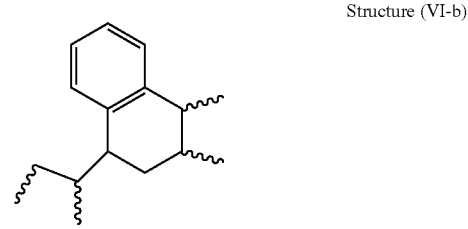

Structure (VI-b)

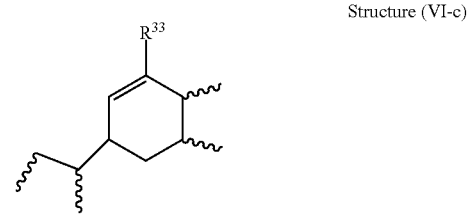

Structure (VI-c)

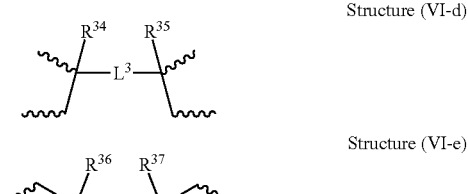

Structure (VI-d)

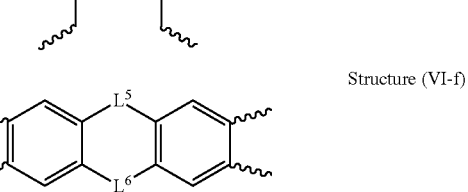

Structure (VI-e)

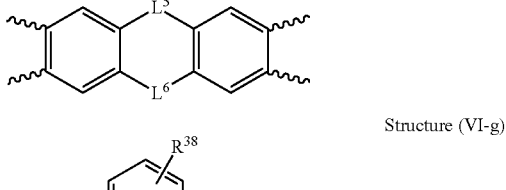

Structure (VI-f)

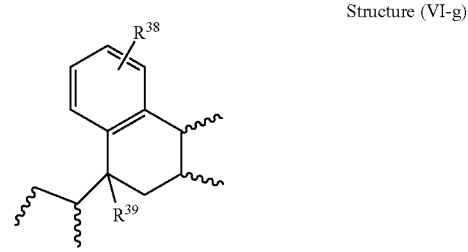

Structure (VI-g)

-continued

Structure (VI-h)

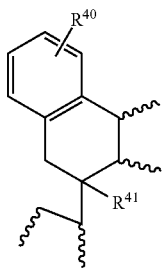

Structure (VI-i)

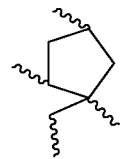

Structure (VI-j)

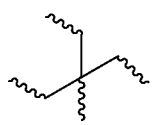

e) a tetravalent group [D¹-L¹-D²] where, D¹ and D² are independently selected from the group consisting of:
1. a substituted or unsubstituted $C_5$-$C_{18}$ monocyclic or polycyclic aliphatic group, and
2. a substituted or unsubstituted $C_6$-$C_{18}$ aryl or heteroaryl group, and L¹ is a divalent linking group selected from the group consisting of:
1. a single bond,
2. a substituted or unsubstituted $C_1$-$C_{20}$ linear, branched, monocyclic or polycyclic alkylene group,
3. a substituted or unsubstituted $C_2$ alkenylene group,
4. a $C_2$ alkynylene group,
5. a substituted or unsubstituted $C_6$-$C_{18}$ aryl or heteroaryl group,
6. an oxygen atom,
7. a sulfur atom,
8. a —(C=O)— group,
9. a —[S(=O)$_2$]— group,
10. a —(S=O)— group,
11. a —[C(=O)O]— group,
12. a —[C(=O)NH]— group, and
13. a —[O(C(R$^{61}$)$_2$(CR$^{62}$)$_2$O)$_{n3}$]— group, where n3 is an integer ranging from 1 to about 6 and $R^{61}$ and $R^{62}$ are independently a hydrogen atom or a substituted or unsubstituted $C_1$-$C_6$ linear or branched alkyl group (e.g., a partially or fully halogen substituted $C_1$-$C_6$ alkyl group).

Examples of divalent linking groups L¹ include, but are not limited to, those shown below, in which n3 is defined above and each of n4 and n5, independently, is an integer ranging from 1 to about 6:

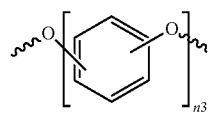

-continued

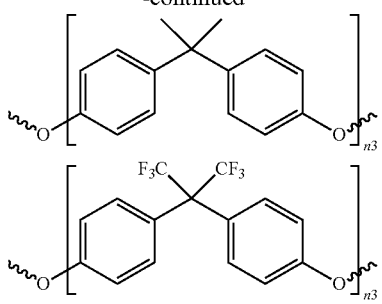

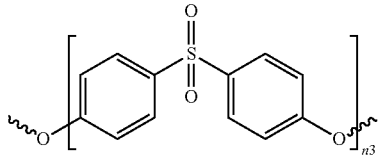

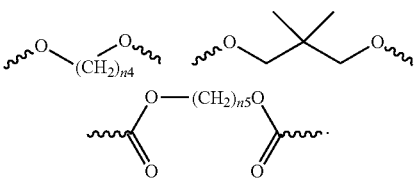

Suitable examples of Y include, but are not limited to, the following moieties:

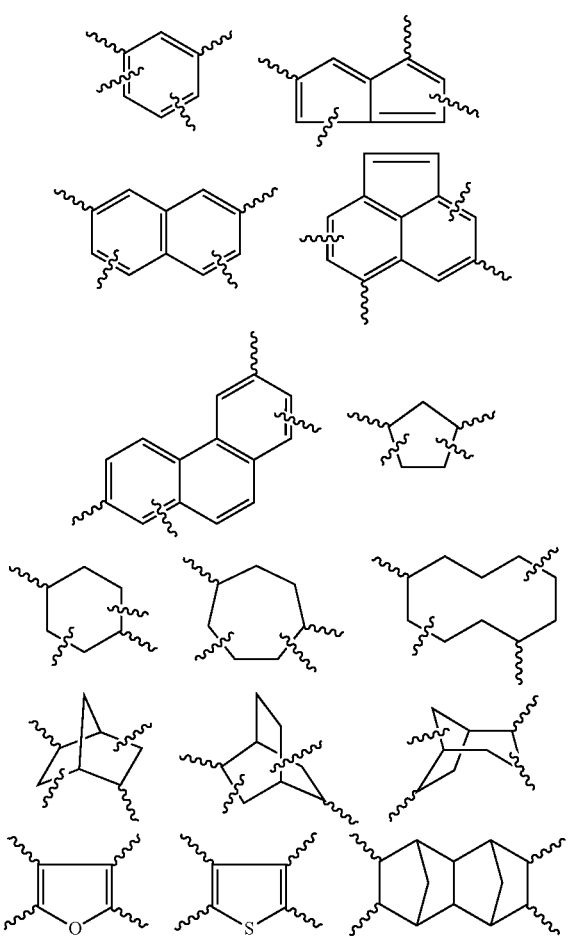

-continued

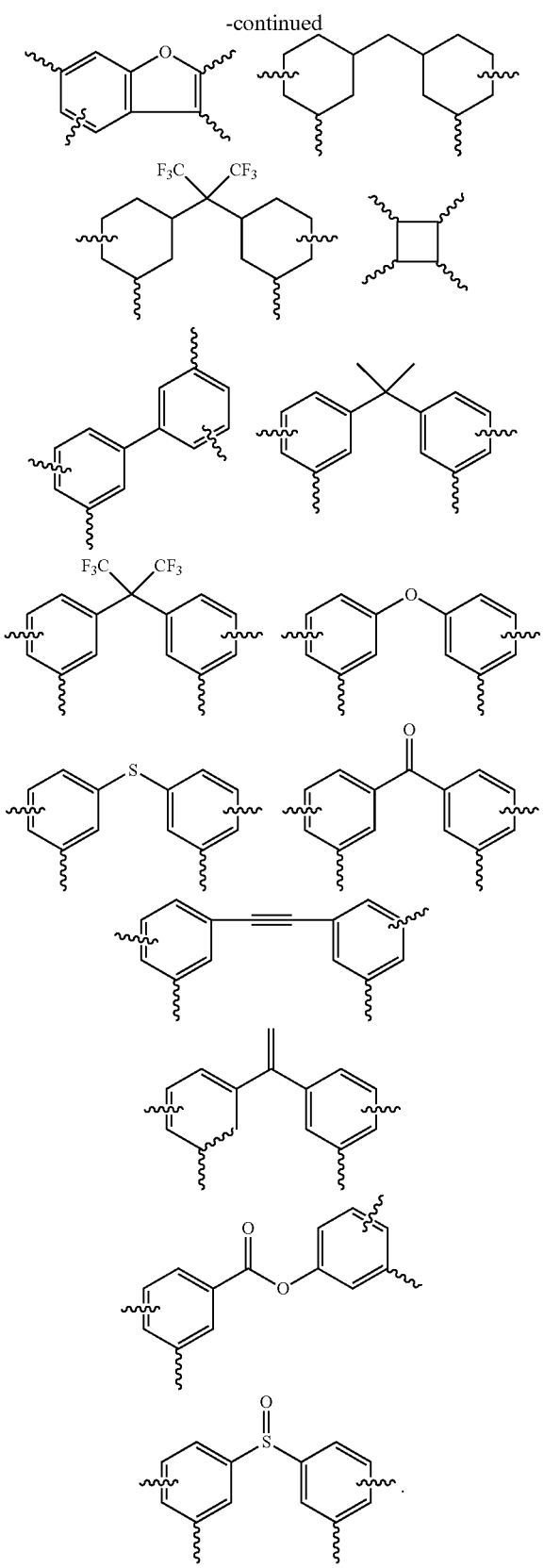

Examples of suitable tetracarboxyic acid dianhydride monomers having the Y moiety include, but are not limited to, pyromellitic dianhydride, benzene-1,2,3,4-tetracarbox- ylic dianhydride, 2,3,5,6-naphthalenetetracarboxylic acid dianhydride, 2,3,6,7-naphthalenetetracarboxylic acid dianhydride, 1,4,5,8-naphthalenetetracarboxylic acid dianhydride, 2,6-dichloronaphthalene-1,4,5,8-tetracarboxylic dianhydride, 2,7-dichloronaphthalene-1,4,5,8-tetracarboxylic dianhydride, 2,3,6,7-tetrachloronaphthalene-1,4,5,8-tetracarboxylic dianhydride, phenanthrene-,8,9,10-tetracarboxylic dianhydride, 3,4,9,10-perylenetetracarboxylic acid dianhydride, pyrazine-2,3,5,6-tetracarboxylic dianhydride, thiophene-2,3,4,5-tetracarboxylic dianhydride, 2,3,5,6-pyridinetetracarboxylic acid dianhydride, butane-1,2,3,4-tetracarboxylic acid dianhydride, 1,2,3,4-cyclopentanetetracarboxylic acid dianhydride, cyclobutane-1,2,3,4-tetracarboxylic acid dianhydride, cyclopentane-1,2,3,4-tetracarboxylic acid dianhydride, cyclohexane-1,2,4,5-tetracarboxylic acid dianhydride, norbornane-2,3,5,6-tetracarboxylic acid dianhydride, bicyclo[2.2.2]oct-7-ene-3,4,8,9-tetracarboxylic acid dianhydride, tetracyclo[4.4.1.0$^{2,5}$.0$^{7,10}$]undecane-1,2,3,4-tetracarboxylic acid dianhydride, 3,3',4,4'-benzophenone tetracarboxylic dianhydride, 2,2',3,3'-benzophenone tetracarboxylic dianhydride, 2,3,3',4'-benzophenone tetracarboxylic dianhydride, 3,3',4,4'-diphenylsulfone tetracarboxylic dianhydride, 2,2',3,3'-diphenylsulfone tetracarboxylic dianhydride, 2,3,3',4'-diphenylsulfone tetracarboxylic dianhydride, 3,3',4,4'-diphenyl ether tetracarboxylic dianhydride, 2,2',3,3'-diphenyl ether tetracarboxylic dianhydride, 2,3,3',4'-diphenyl ether tetracarboxylic dianhydride, 2,2-[bis(3,4-dicarboxyphenyl)] hexafluoropropane dianhydride, ethyleneglycol bis(anhydrotrimellitate), and 5-(2,5-dioxotetrahydro)-3-methyl-3-cyclohexene-1,2-dicarboxylic anhydride.

Examples of preferred tetracarboxylic acid dianhydride monomers having the Y moiety include, but are not limited to, pyrazine-2,3,5,6-tetracarboxylic dianhydride, thiophene-2,3,4,5-tetracarboxylic dianhydride, 2,3,5,6-pyridinetetracarboxylic acid dianhydride, norbornane-2,3,5,6-tetracarboxylic acid dianhydride, bicyclo[2.2.2]oct-7-ene-3,4,8,9-tetracarboxylic acid dianhydride, tetracyclo[4.4.1.0$^{2,5}$.0$^{7,10}$] undecane-1,2,3,4-tetracarboxylic acid dianhydride, 3,3',4,4'-benzophenone tetracarboxylic dianhydride, 3,3',4,4'-diphenylsulfone tetracarboxylic dianhydride, 3,3',4,4'-diphenyl ether tetracarboxylic dianhydride, 2,3,3',4'-diphenyl ether tetracarboxylic dianhydride, 2,2-[bis(3,4-dicarboxyphenyl)] hexafluoropropane dianhydride, ethyleneglycol bis(anhydrotrimellitate), and 5-(2,5-dioxotetrahydro)-3-methyl-3-cyclohexene-1,2-dicarboxylic anhydride.

In some embodiments, examples of tetracarboxylic acid dianhydride monomers include:

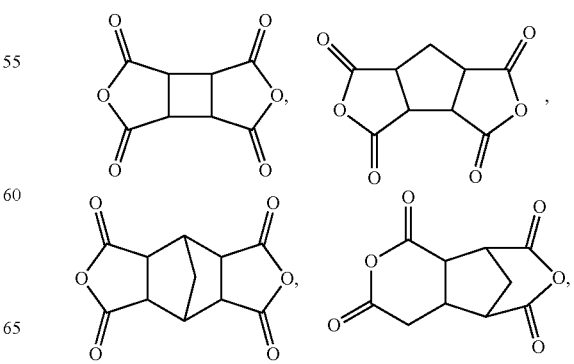

-continued

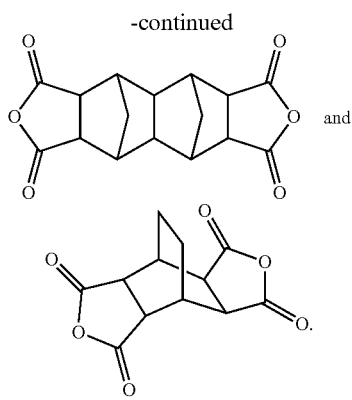
and

In some embodiments, the diamines of Structures (Ia) and/or Structures (Ib) and Structure (II) are reacted with at least one tetracarboxylic acid dianhydride to yield a polyamic acid of Structure (VII):

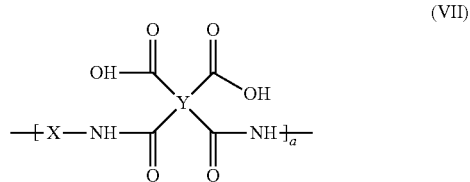
(VII)

in which at least some of X are Structure $X^{1a}$ and/or $X^{1b}$, and at least some of X are $X^2$:

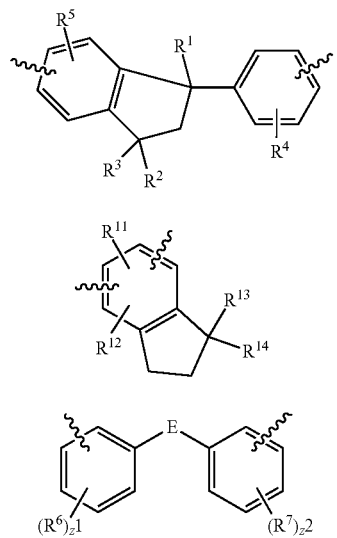

$X^{1a}$ $X^{1b}$ $X^2$

In Structures $X^{1a}$, $X^{1b}$, and $X^2$, $R^1$-$R^7$ and $R^{11}$-$R^{14}$, $z^1$ and $z^2$ are those defined above.

The polyamic acid of Structure (VII) can be synthesized by numerous synthetic procedures or variations of those procedures known to those skilled in the art. In general, a polyamic acid of Structure (VII) can be formed through a condensation polymerization reaction between one or more diamines and one or more tetracarboxylic acid dianhydrides. For example, one can bring one or more diamines in contact with one or more tetracarboxylic acid dianhydrides in the presence of a solvent suitable to dissolve the monomers and, preferably, the resultant polyamic acid.

In some embodiments, to prepare a polyamic acid, the diamine component and tetracarboxylic acid dianhydride component are charged into a reaction vessel at the same time or by charging one of the components in the form of solid or solution into a solution of the other component (complete dissolution of all materials might not occur). Charging both the components at the same time is advantageous in view of the productivity because the time required for charging is shortened. Generally, the condensation polymerization reaction between the diamine component and tetracarboxylic acid dianhydride component can be carried out at about 15° C. to about 80° C. for about 1 to about 48 hours.

Suitable polymerization solvents useful in the present invention include, but are not limited to, N-methyl-2-pyrrolidone, N,N-dimethylformamide, dimethylsulfoxide, gamma-butyrolactone, N,N-dimethylacetamide, tetramethylene sulfone, p-chlorophenol, m-cresol, diethyleneglycol methyl ether, methyl-3-methoxyproprionate, ethyl-3-ethoxypropionate, cyclohexanone, propylene glycol monomethyl ether acetate, and 2-chloro-4-hydroxytoluene. These solvents can be used singly or in combination of two or more. Of these solvents, preferred are N-methyl-2-pyrrolidone, gamma-butyrolactone and N,N-dimethylacetamide, with N-methyl-2-pyrrolidone being more preferred. In some embodiments, a poor solvent for the polyimide can be used in combination with these solvents in such an amount to not allow the polyamic acid to precipitate. Examples of such a poor solvent include hexane, heptane, benzene, toluene, xylene, chlorobenzene and o-dichlorobenzene. The amount of the poor solvent to be used is preferably 50 percent by weight or less (inclusive of zero) based on the total amount of the solvents. The polyamic acid thus produced can be isolated by precipitation into a non-solvent or a poor solvent and collected by filtration.

In some embodiments, the molar ratio of diamine component(s) to tetracarboxylic acid dianhydride component(s) can be greater than 1.00. The resulting species is an amino-terminated polyamic acid (e.g., a polyamic acid of Structure (VIIa)). The molar ratio of diamine component(s) to tetracarboxylic acid dianhydride component(s) can generally range from 1.01 to 1.40. In some embodiments, a molar ratio of diamine to tetracarboxylic acid dianhydride of about 1.05 to 1.33 is employed. In some embodiments, a molar ratio of diamine to tetracarboxylic acid dianhydride of about 1.05 to 1.25 is employed. In some embodiments, a molar ratio of diamine to tetracarboxylic acid dianhydride of about 1.05 to 1.20 is employed.

Structure (VIIa)

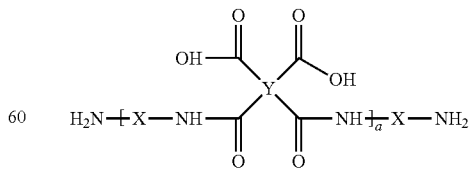

When an excess of tetracarboxylic acid dianhydride to diamine is employed, the suitable molar ratio of diamine to tetracarboxylic acid dianhydride ranges from about 0.8 to about 0.99. A preferred molar ratio of diamine to tetracarboxylic acid dianhydride ranges from about 0.83 to about 0.98. In some embodiments, the preferred molar ratio of diamine to tetracarboxylic acid dianhydride ranges from about 0.87 to about 0.98. In some embodiments, the preferred molar ratio diamine to tetracarboxylic acid dianhydride ranges from about 0.91 to about 0.98. When a molar excess of tetracarboxylic acid dianhydride is employed, an anhydride-terminated polyamic acid (e.g., a polyamic acid of Structure (VIIb)) is produced.

Structure (VIIb)

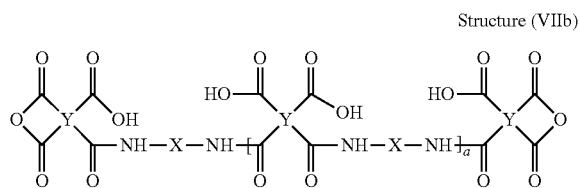

Those skilled in the art will understand that there are multiple synthetic pathways to convert polyamic acids of Structures (VIIa) and (VIIb) to the polyimide polymers of this disclosure. One pathway is to imidize polyamic acids of Structures (VIIa) and (VIIb) using chemical or thermal imidization techniques to form polyimide of Structure (VIIIa) or (VIIIb). This reaction can then be followed by an endcapping reaction of the terminal group (e.g., the terminal $NH_2$ in Structure (VIIa) and the terminal anhydride in Structure (VIIb)) with a compound having a first functional group which is reactive with the terminal group, and at least one second functional group selected from a substituted or unsubstituted alkenyl group and a substituted or unsubstituted alkynyl group. Alternatively, the endcapping reaction of the terminal group in Structure (VIIa) or (VIIb) can be done first, followed by the chemical or thermal imidization.

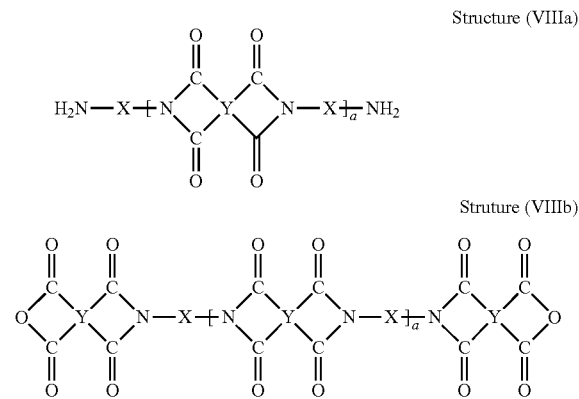

Structure (VIIIa)

Struture (VIIIb)

Another synthetic pathway is to include in the polymerization reaction a monoamine or monoanhydride containing an additional functional group selected from a radical sensitive group, an acid reactive group or a functional group that does not interfere with the condensation reaction that can be functionalized later. In such embodiments, the end-capping reaction is performed together with the imidization reaction.

The thermal imidization can, for example, be performed in the solid state at a temperature ranging from about 100° C. to about 400° C. (e.g., from about 200° C. to about 300° C., or about 250° C.). In another embodiment, the thermal imidization can be performed in a solution at a temperature ranging from about 100° C. to about 250° C. When the heat treatment is performed within this temperature range, the imidization reactivity can be controlled within a desired range, minimizing non-reacted polyamic acid. In some embodiments, the thermal imidization in this manner is best done before reaction of the polymer terminal groups.

The polyamic acid can also be dehydrated using an azeotroping thermal procedure. An example of this reaction is described in U.S. Pat. No. 5,478,915. For example, after the synthesis of the polyamic acid is complete, toluene is added, and the solution is azeotropically refluxed at 155° C., collecting the water in a Dean-Stark trap.

In some embodiments, the polyimide of Structure (VIIIa) or (VIIIb) is produced by chemical imidization. For example, a chemical imidizing agent (e.g., a dehydrating agent) can be added to the polyamic acid of Structure (VIIa) or (VIIb). This chemical imidization agent can catalyze the ring-closing dehydration process of the polyamic acid groups to form imide functionalities on the polymer backbone. If the polyamic acid is isolated after the synthesis, it can be re-dissolved in a compatible solvent. Normally, when a chemical imidization is employed, the imidization reaction takes place without isolation of the polyamic acid.

A suitable dehydrating agent can be used alone or in combination with a non-nucleophilic base to imidize the polyamic acid. Examples of suitable dehydrating agents include, but are not limited to, trifluoromethane sulfonic acid, methanesulfonic acid, p-toluenesulfonic acid, ethanesulfonic acid, butanesulfonic acid, perfluorobutanesulfonic acid, acetic anhydride, propionic anhydride, and butyric anhydride. If used, the non-nucleophilic base employed can be the same as or different from the non-nucleophilic base employed in the end-capping reaction. Examples of suitable non-nucleophilic bases include, but are not limited to, pyridine, triethylamine, tripropylamine, tributylamine, dicyclohexylmethylamine, 2-methylpyridine, 2,6-lutidine, 3,5-lutidine, picoline, 4-dimethylaminopyridine (DMAP) and the like.

In some embodiments, the chemical imidization process is carried out with a suitable dehydrating reagent and a non-nucleophilic base at about 60° C. to about 130° C. for about 6 hours to about 48 hours. The dehydrating agent and non-nucleophilic base can be employed in equimolar concentrations. In another embodiment, the molar ratio of dehydrating agent to non-nucleophilic base is from about 1.1 to about 10 (e.g., from about 1.25 to 5, or from about 1.5 to about 3.0). In one embodiment, about 90 mole % to 200 mole % of a dehydrating agent based on the total amount of the polyamic acid present in the mixture is used to complete the imidization reaction. Preferably, 100 mole % to 160 mole % of a dehydrating agent is used to complete the imidization process.

Imidization to form a polyimide of Structure (VIIIa) or (VIIIb) can be confirmed by observation of characteristic absorptions in the infrared spectrum from 1770 and 1700 $cm^{-1}$ attributable to the imide ring structure. In some embodiments, the polymers of this disclosure are at least about 90% (e.g., at least about 95%, at least about 98%, at least about 99, or about 100%) imidized.

The terminal $NH_2$ groups of the polymers of Structures (VIIa) and (VIIIa) can be optionally end-capped by reaction with an end-capping compound having a first functional group which is reactive to an amine, and having at least one second functional group selected from a substituted or unsubstituted alkenyl group (e.g., a $C_2$-$C_6$ alkenyl group) and a substituted or unsubstituted alkynyl group (e.g., a $C_2$-$C_6$ alkynyl group). Examples of such end-capping compounds include, but are not limited to, acid chloride compounds, dicarboxylic acid anhydrides, epoxide compounds, and isocyanate compounds also containing at least one second functional group selected from a substituted or unsubstituted alkenyl group and a substituted or unsubstituted alkynyl group. Examples of substituted alkenyl groups include, but are not limited to, acrylates, methacrylates, stilbenes, and vinyl ethers. Examples of substituents on alkynyl groups include, but are not limited to, alkyl (e.g., Me or Et), aryl (e.g., phenyl or substituted phenyl), alkanoyl (e.g., acetyl) and aroyl (e.g., benzoyl).

Examples of end-capping compounds having a first functional group reactive to the terminal NH$_2$ groups that also have at least one second functional group selected from a substituted or unsubstituted alkenyl group and a substituted or unsubstituted alkynyl group include, but are not limited to, the following compounds:

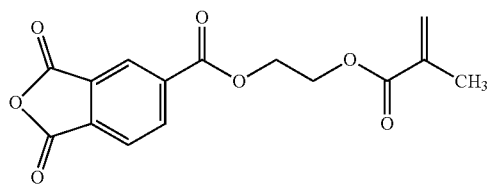

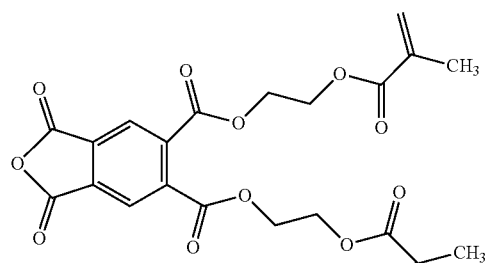

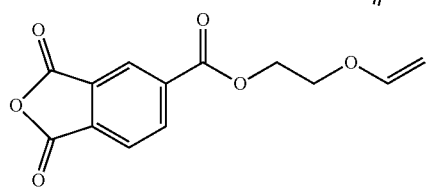

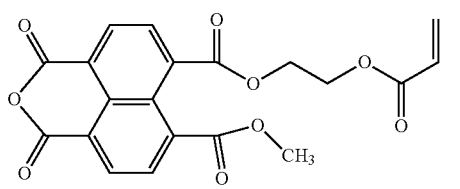

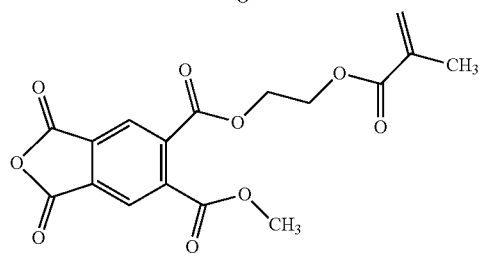

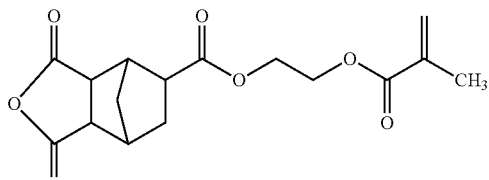

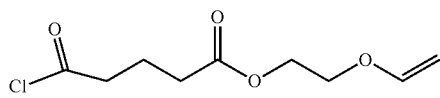

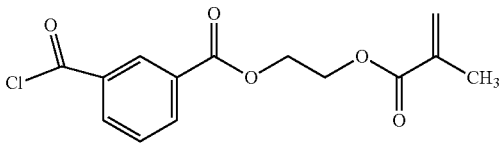

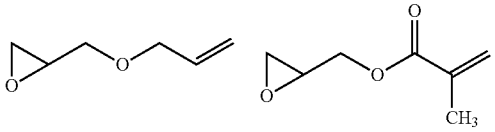

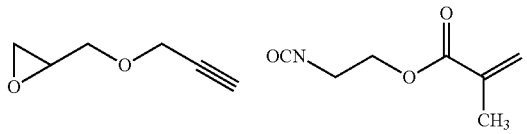

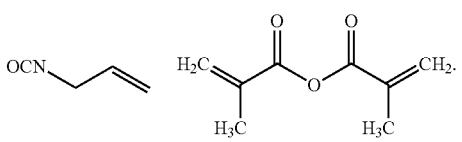

When anhydrides are employed as the reactive functional group to endcap the polymers of Structures (VIIa) and (VIIIa), polyamic acids are produced. Polyamic acids terminating polymers of Structure (VIIa) can be imidized when the backbone polyamic acids are imidized. Polyamic acids terminating polymers of Structure (VIIIa) can imidize spontaneously or during isolation and drying, or can easily be imidized with mild heat or with a minimal of dehydrating agent.

The terminal anhydride groups of the polymers of Structures (VIIb) and (VIIIb) can be end-capped by reaction with a compound having a first functional group which is reactive with an anhydride, and having at least one second functional group selected from a substituted or unsubstituted alkenyl group and a substituted or unsubstituted alkynyl group. Examples of such compounds include, but are not limited to, amine compounds, alcohols, and thiols also containing at least one second functional group selected from a substituted or unsubstituted alkenyl group and a substituted or unsubstituted alkynyl group.

Examples of suitable end-capping compounds containing reactive groups meeting these criteria include, but are not limited to, the following compounds:

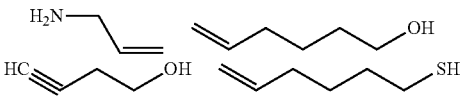

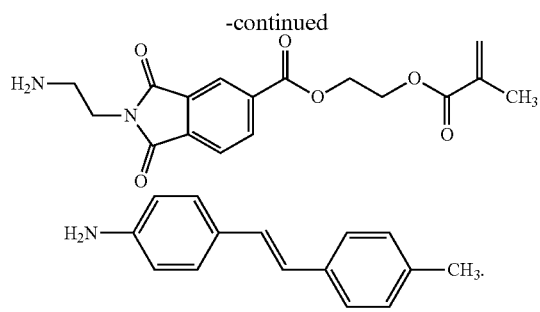

In some cases, a non-nucleophilic base can be used to facilitate the reaction with the terminal anhydride groups. Examples of suitable non-nucleophilic bases include, but are not limited to, pyridine, triethylamine, tripropylamine, tributylamine, dicyclohexylmethylamine, 2-methylpyridine, 2,6-lutidine, 3,5-lutidine, picoline, 4-dimethylaminopyridine (DMAP) and the like.

When the polymers of Structures (VIIb) and (VIIIb) are endcapped with an amine containing compound, a polyamic acid is produced. In this situation, when the polymers of Structure (VIIb) are imidized, the endcap is imidized as well. The polyamic acid resulting from the end-capping of polymers of Structure (VIIIb) with an amine containing compound can be isolated. Alternatively, the terminal polyamic acid can be imidized thermally or chemically during or after the formation of the polyimide.

In some embodiments, the resulting polyimides of the present disclosure can be isolated by precipitation into water and/or an organic solvent, recovered by filtration, and dried. In another embodiment, an indane-containing polyimide of the present disclosure can be isolated by addition of its solution to a combination of water and a suitable water-immiscible solvent. Because of the lower polarity nature of the indane moieties in the polyimide polymer, higher solubility in lower polarity water immiscible solvents allows the polyimide of this disclosure, unlike most polyimides, to be extracted from the higher polarity reaction solvent/water mixture. This extracted polymer solution can be purified by washing with water followed by separation of the water layer, distillation of various volatile compounds, and subsequent extraction into a higher boiling solvent.

The polyimides of this disclosure generally have a CTE of less than about 120 ppm/° C., preferably less than about 80 ppm/° C. and more preferably less than about 60 ppm/° C. and are soluble in organic solvents such as gamma-butyrolactone (GBL), cyclopentanone (CP) and dimethyl sulfoxide (DMSO) and mixtures thereof. In one embodiment, the polyimides of this disclosure have a CTE of about 50 ppm/° C. to about 70 ppm/° C. In one embodiment, the polyimides of this disclosure have a CTE of about 40 ppm/° C. to about 60 ppm/° C. In one embodiment, the polyimides of this disclosure have a CTE of less than about 40 ppm/° C. In addition, generally, the polyimide polymers of this disclosure have solubility from about 20 grams/100 grams of solvent to about 40 grams/100 grams of a solvent, where the solvent can be GBL, CP, DMSO and/or mixtures thereof.

The polyimides of this disclosure generally have a weight average molecular weight (measured using a polystyrene standard using a GPC) of from 2000 Daltons to 100,000 Daltons, preferable from 6000 Daltons to 40,000 Daltons, more preferably from 8000 Daltons to 30,000 Daltons.

Polyimide-Containing Compositions

In some embodiments, this disclosure features compositions (e.g., photosensitive compositions) comprising:

(A) at least one polyimide polymer containing the reaction product (e.g., a condensation and imidization product) of components (a), (b), (c), and optionally (d) as described above;
(B) at least one reactive functional compound (RFC) having at least one functional group capable of reacting with a substituted or unsubstituted alkenyl group and a substituted or unsubstituted alkynyl group on the polyimide polymer;
(C) an initiator capable of initiating a reaction between the substituted or unsubstituted alkenyl group and a substituted or unsubstituted alkynyl group on the polyimide polymer and the RFC (e.g., in the presence of heat, light, or other radiation); and
(D) at least one solvent.

The reactive functional compound (RFC) in component (B) generally possesses at least one functional group capable of reacting with the terminal functional group on the polyimide polymer (e.g., the second functional group on the polyimide polymer described above). The RFC can be a monomer or an oligomer. The oligomer can contain many monomer units and is capable of further reactions to be incorporated in the final material. Examples of such monomer units/oligomers are based on one or more of the following types: acrylate, ester, vinyl alcohol, urethane, urea, imide, amide, carboxazole, carbonate, pyranose, siloxane, urea-formaldehyde and melamine-formaldehyde. The RFC generally contains at least one terminal and/or pendant reactive functional group capable of radical, thermal, or acid catalyzed reaction with the at least one second functional group selected from a substituted or unsubstituted alkenyl group and a substituted or unsubstituted alkynyl group on the polyimide polymer. In one embodiment, the reactive functional group on the RFC includes a double or triple bond.

Suitable examples of reactive functional groups on the RFC include, but are not limited to, a vinyl group, an allyl group, a vinyl ether group, a propenyl ether group, a (meth)acryloyl group, an epoxy group, a —SiH group and a —SH (thiol) group.

In one embodiment, a suitable example of an RFC includes, but is not limited to, a urethane acrylate oligomer. The term urethane acrylate oligomer refers to a class of compounds that contain urethane linkages and have (meth) acrylate (e.g., acrylate or methacrylate) functional groups such as urethane multi(meth)acrylate, multiurethane (meth) acrylate, and multiurethane multi(meth)acrylate. Types of urethane (meth)acrylate oligomers have been described by, for example, Coady et al., U.S. Pat. No. 4,608,409 and by Chisholm et al., U.S. Pat. No. 6,844,950. Other specific examples of RFCs include 1,6-hexanediol di(meth)acrylate, tetraethyleneglycol di(meth)acrylate, divinylbenzene, ethoxylated bisphenol-A-di(meth)acrylate, diethylene glycol bis(allyl carbonate), trimethylolpropane tri(meth)acrylate, ditrimethylolpropane tetra(meth)acrylate, pentaerythritol tri(meth)acrylate, pentaerythritol tetra(meth)acrylate, dipentaerythritol penta-/hexa-(meth)acrylate, isocyanurate tri(meth)acrylate, bis(2-hydroxyethyl)-isocyanurate di(meth)acrylate, 1,3-butanediol tri(meth)acrylate, 1,4-butanediol tri(meth)acrylate, methyl (meth)crylate, butyl (meth)crylate, cyclohexyl (meth)acrylate, benzyl(meth)acrylate, neopentyl glycol di(meth)acrylate, (meth)acrylate modified-urea-formaldehyde resins, (meth)acrylate modified melamine-formaldehyde resins and (meth)acrylate modified cellulose.

Examples of RFC compounds containing thiol groups include, but are not limited to, trimethylolpropane tris(mercaptoacetate), pentaerythritol tetrakis(mercaptoacetate), dipentaerythritol hexakis(3-mercaptopropionate), and ethoxylated trimethylolpropane tri-3-mercaptopropionate. Examples of RFC compounds containing vinyl ether groups include, but are not limited to 1,4-butanediol divinyl ether, 1,4-cyclohexanedimethanol divinyl ether, di(ethylene glycol) vinyl ether, poly(ethylene glycol) divinyl ether, and bis[4-(vinyloxy)butyl] (4-methyl-1,3-phenylene)biscarbamate. One example of a RFC compound containing a SiH group is octasilane POSS® SH1310 available from Hybrid Plastics. Examples of RFC compounds containing epoxide groups include, but are not limited to, ethylene glycol diglycidyl ether and 1,4-butanediol diglycidyl ether.

The initiator (e.g., photoinitiator) in component (C) used in the composition is a compound that is capable of initiating a reaction between the second functional group on the polyimide polymer and the reactive functional compound, when the composition or a portion of the composition is exposed to light and/or heat. Some initiators used in the composition function by generating free radicals when heated or by absorbing light at the wavelength of exposure. Other initiators used in the composition function by generating acid when heated or by absorbing light at the wavelength of exposure. Other initiators used in the composition function by generating a basic compound when heated or by absorbing light at the wavelength of exposure. An example of a free-radical photoinitiator is 1-hydroxy-cyclohexyl-phenyl-ketone (Irgacure 184) from BASF. An example of a photoactive initiator is a photoacid generator such as triphenyl sulfonium triflate from Aldrich Catalog No. 526940. In some embodiments, the initiators described herein can also catalyze the reaction between the second functional group on the polyimide polymer and the reactive functional compound and therefore also serves as a catalyst.

Specific examples of initiators that generate free radicals when heated include, but are not limited to, benzoyl peroxide, cyclohexanone peroxide, lauroyl peroxide, tert-amyl peroxybenzoate, tert-butyl hydroperoxide, dicumyl peroxide, cumene hydroperoxide, succinic acid peroxide, di(n-propyl)peroxydicarbonate, 2,2-azobis(isobutyronitrile), 2,2-azobis(2,4-dimethylvaleronitrile), dimethyl-2,2-azobisisobutyrate, 4,4-azobis(4-cyanopentanoic acid), azobiscyclohexanecarbonitrile, 2,2-azobis(2-methylbutyronitrile) and the like.

Specific examples of initiators that generate free radicals when exposed to high energy radiation (also known as photoinitiators) include, but are not limited to, NCI-831 (Available from ADEKA Corp.), 1,8-octanedione, 1,8-bis[9-(2-ethylhexyl)-6-nitro-9H-carbazol-3-yl]-1,8-bis(O-acetyloxime), 2-hydroxy-2-methyl-1-phenylpropan-1-one, 1-hydroxycyclohexyl phenyl ketone (Irgacure 184 from BASF), a blend of 1-hydroxycyclohexylphenylketone and benzophenone (Irgacure 500 from BASF), 2,4,4-trimethylpentyl phosphine oxide (Irgacure 1800, 1850, and 1700 from BASF), 2,2-dimethoxy-2-acetophenone (Irgacure 651 from BASF), bis(2,4,6-trimethyl benzoyl)phenyl-phosphine oxide (Irgacure 819 from BASF), 2-methyl-1-[4-(methylthio)phenyl]-2-morphorinopropane-1-on (Irgacure 907 from BASF), (2,4,6-trimethylbenzoyl)diphenyl phosphine oxide (Lucerin TPO from BASF), ethoxy(2,4,6-trimethylbenzoyl) phenyl phosphine oxide (Lucerin TPO-L from BASF), a blend of phosphine oxide, hydroxy ketone and a benzophenone derivative (ESACURE KTO46 from Sartomer), 2-hydroxy-2-methyl-1-phenylpropane-1-on (Darocur 1173 from Merck), benzophenone, 2-chlorothioxanthone, 2-methylthioxanthone, 2-isopropylthioxanthone, benzodimethyl ketal, 1,1,1-trichloroacetophenone, diethoxyacetophenone, m-chloroacetophenone, propiophenone, anthraquinone, dibenzosuberone and the like.

Specific examples of nonionic-type photoactive initiators are (5-toluylsulfonyloxyimino-5H-thiophen-2-ylidene)-2-methylphenyl-acetonitrile(Irgacure 121 from BASF), phenacyl p-methylbenzenesulfonate, benzoin p-toluenesulfonate, (p-toluene-sulfonyloxy)methylbenzoin, 3-(p-toluenesulfonyloxy)-2-hydroxy-2-phenyl-1-phenylpropyl ether, N-(p-dodecylbenzenesulfonyloxy)-1,8-naphthalimide, N-(phenylsulfonyloxy)-1,8-napthalimide, bis(cyclohexylsulfonyl) diazomethane, 1-p-toluenesulfonyl-1-cyclohexylcarbonyldiazomethane, 2-nitrobenzyl p-toluenesulfonate, 2,6-dinitrobenzyl p-toluenesulfonate, and 2,4-dinitrobenzyl p-trifluoromethylbenzenesulfonate and the like.

Specific examples of ionic-type photoactive initiators are triphenyl sulfonium methanesulfonate, triphenyl sulfonium trifluoromethanesulfonate, triphenyl sulfonium nonafluorobutanesulfonate, triphenyl sulfonium perfluorooctanesulfonate, triphenyl sulfonium 4-methyl phenyl sulfonate, 4-methylphenyl-diphenyl sulfonium nonafluorobutanesulfonate, triarylsulfonium bis(trimethylsulfonyl)imide, triarylsulfonium tris(trimethylsulfonyl)methide, diphenyl iodonium hexafluoropropane sulfonate, diphenyl iodonium 4-methylphenyl sulfonate, bis(4-tert-butylphenyl)iodonium trifluoromethane sulfonate, bis(4-tert-butylphenyl)iodonium hexafluoromethane sulfonate, and bis(4-cyclohexylphenyl) iodonium trifluoromethane sulfonate and the like.

Suitable solvents (D) useful in the compositions of this disclosure can include alcohols, ketones, lactones, ethers, amides, imides and esters. The solvent typically should dissolve all components of the composition, cast a good film and should not interfere with the combining reaction (e.g., crosslinking reaction between components (A) and (B)) of the composition. Suitable examples of organic solvents include, but are not limited to, gamma-butyrolactone (GBL), N-methyl-2-pyrrolidone (NMP), dimethylimidazolidinone, N-methylcaprolactam, N-methylpropionamide, N,N-dimethylacetamide (DMAc), dimethyl sulfoxide (DMSO), N,N-dimethylformamide (DMF), N,N-diethylformamide, diethylacetamide, methyl ethyl ketone (MEK), methyl isobutyl ketone (MIBK), 2-heptanone, cyclopentanone (CP), cyclohexanone, n-butyl acetate (nBA), propylene glycol methyl ether acetate (PGMEA), propylene glycol methyl ether (PGME), ethyl lactate (EL), propyl lactate, 3-methyl-3-methoxybutanol, tetralin, isophorone, ethylene glycol monobutyl ether, diethylene glycol monoethyl ether, diethylene glycol monoethyl ether acetate, diethylene glycol dimethyl ether, diethylene glycol methylethyl ether, triethylene glycol monoethyl ether, dipropylene glycol monomethyl ether, methyl 3-methoxypropionate, ethyl 3-ethoxypropionate, diethyl malonate, ethylene glycol 1,4:3,6-dianhydrosorbitol, 2,5-dimethyl ether (2,5-dimethylisosorbide), 1,4:3,6-dianhydrosorbitol 2,5-diethyl ether (2,5-diethylisosorbide) and mixtures thereof. Preferred solvents are gamma-butyrolactone (GBL), cyclopentanone (CP), cyclohexanone, 2,5-dimethyl ether (2,5-dimethylisosorbide), ethyl lactate (EL) and dimethylsulfoxide (DMSO). These solvents can be used individually or in combination.

In some embodiments, the amount of polyimide (A) is preferably from about 2 to about 50 weight %, more preferably from about 5 to about 45 weight %, still more preferably from about 10 to about 40 weight %, based on the entire weight of the composition.

In some embodiments, the amount of component (B) having at least one reactive functional group is preferably from about 1 to about 25 weight %, more preferably from about 2 to about 20 weight %, still more preferably from about 5 to about 15 weight %, based on the entire weight of the composition.

In some embodiments, the amount of component (C) is preferably from about 0.0001 to about 20 weight %, more preferably from about 0.01 to about 15 weight %, still more preferably from about 1 to about 10 weight %, based on the entire weight of the composition.

In some embodiments, the amount of component (D) is preferably from about 40 to about 98 weight %, more preferably from about 50 to about 95 weight %, still more preferably from about 60 to about 90 weight %, based on the entire weight of the composition.

Other additives such as adhesion promoters, surfactants, and plasticizers, but are not limited to these, can be added to the composition of this disclosure. The amount of additional additives can range from 0% to about 15% based on the entire weight of the composition.

Suitable adhesion promoters are described in "Silane Coupling Agent" Edwin P. Plueddemann, 1982 Plenum Press, New York. Classes of adhesion promoters include, but are not limited to, vinylalkoxysilanes, methacryloxy-alkoxyysilanes (e.g. 3-methacryl-oxypropyldimethoxy-methylsilane, and 3-methacryloxypropyltrimethoxysilane), mercaptoalkoxysilanes, aminoalkoxysilanes, epoxyalkoxysilanes and glycidyloxyalkoxysilanes.

Examples of suitable adhesion promoters which can be employed in the compositions of this disclosure can be described by Structure (XIV):

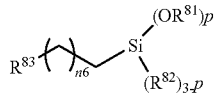

Structure (XIV)

in which each $R^{81}$ and $R^{82}$ independently is a substituted or unsubstituted $C_1$-$C_{10}$ linear or branched alkyl group or a substituted or unsubstituted $C_3$-$C_{10}$ cycloalkyl group, p is an integer from 1 to 3, n6 is an integer from 1 to 6, $R^{83}$ is one of the following moieties:

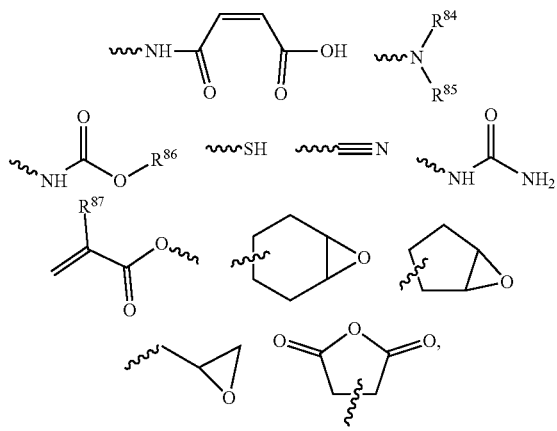

in which each $R^{84}$, $R^{85}$, $R^{86}$ and $R^{87}$, independently, is a $C_1$-$C_4$ alkyl group or a $C_5$-$C_7$ cycloalkyl group. Preferred adhesion promoters are those (including methacrylate/acrylate) in which $R^{83}$ is selected from:

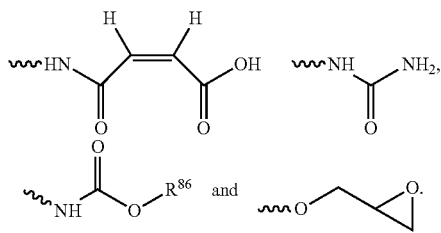

Examples of suitable adhesion promoters having Structure (XIV) include, but are not limited to, gamma-aminopropyltrimethoxysilane, gamma-glycidyloxypropylmethyldimethoxysilane, gamma-glycidyloxypropylmethyldiethoxysilane, glycidyloxypropyltrimethoxysilane, and gamma-mercaptopropylmethyldimethoxysilane.

In some embodiments, the adhesion promoter contains a silicon compound without a thiol group. In some embodiments, the adhesion promoter contains a silicon compound without an acrylic moiety. In some embodiments, the adhesion promoter contains a silicon compound without an epoxy group.

The concentration of the optional adhesion promoter, if employed, ranges from about 0.1 wt % to about 5 wt % of total weight of the composition. A preferred amount of adhesion promoter is from about 0.2 wt % to about 1.5 wt %. A more preferred amount of adhesion promoter is from about 0.3 wt % to about 1 wt %.

The compositions of this disclosure can also optionally contain at least one surfactant. If a surfactant is employed, it can be added from about 0.001 to about 2 wt % and preferably from about 0.01 to about 1 wt % based on total weight of the compositions of this disclosure. Examples of suitable surfactants include, but are not limited to, the surfactants described in JP-A-62-36663, JP-A-61-226746, JP-A-61-226745, JP-A-62-170950, JP-A-63-34540, JP-A-7-230165, JP-A-8-62834, JP-A-9-54432 and JP-A-9-5988.

The compositions of the present disclosure can optionally contain at least one plasticizer. The concentration of the optional plasticizer, if employed, can range from about 1 wt % to about 10 wt % of total weight of the composition. A preferred amount of plasticizer can be from about 2 wt % to about 10 wt %.

In some embodiments, the compositions described above can be used to prepare a polymeric layer in the dry film structure described herein. Such compositions can further include at least one nanoparticle (e.g., a plurality of nanoparticles). The nanoparticle can be made from one or more polymers, inorganic materials, and/or metals. The nanoparticles suitable for this application are preferably less than 200 μm in diameter and are compatible with the other components of the compositions of this disclosure. Examples of such nanoparticles are found, e.g., in U.S. Pat. Nos. 6,291,070 and 6,844,950, the contents of which are hereby incorporated by reference. Without wishing to be bound by theory, it is believed that the nanoparticles can improve the mechanical properties (e.g., CTE) and electrical properties (e.g., dielectric properties) of the polymeric layer of the dry film structure.

Examples of nanoparticles include silica, alumina, titania, zirconia, hafnium oxide, CdSe, CdS, CdTe, CuO, zinc oxide, lanthanum oxide, niobium oxide, tungsten oxide, strontium oxide, calcium titanium oxide, sodium titanate, and potassium niobate. The nanoparticles can be surface treated or untreated nanoparticles.

In some embodiments, the compositions of the present disclosure include a second polymer which forms a continuous phase with the polyimide polymer described above. In some embodiments, the compositions of the present disclosure are substantially free of a polymer which forms a discontinuous phase with the polyimide polymer described above.

The present disclosure also features a process of using the compositions described herein for various purposes. For example, in some embodiments, to form a coated substrate, the process can include the following the steps:
a) coating a substrate with a composition of the present disclosure to form a coated substrate having a film (e.g., a tacky film) on the substrate, and
b) baking the coated substrate (e.g., at a temperature from about 50° C. to about 200° C.) to form a coated substrate having a dried film.

In some embodiments, to form a non-patterned coating substrate, the process can include the following steps:
a) coating a substrate with a composition of the present disclosure to form a coated substrate having a film (e.g., a tacky film) on the substrate;
b) baking the coated substrate (e.g., at a temperature from about 50° C. to about 150° C.) in a first baking step to form a coated substrate having a dried film;
c) exposing the dried film to heat or radiation to form a coated substrate having a dried, exposed film, and
d) optionally, baking the coated substrate having a dried, exposed film (e.g., at a temperature from about 50° C. to about 200° C.) in a second baking step.

In some embodiments, the process is a lithographic process to prepare patterned relief images using the compositions described herein. In such embodiments, the compositions described herein can be used as negative photosensitive resin compositions. In such embodiments, the process can include:
a) coating a substrate with a composition of the present disclosure to form a coated substrate having a film (e.g., a tacky film) on the substrate;
b) baking the coated substrate (e.g., at a temperature from about 50° C. to about 150° C.) in a first baking step to form a coated substrate with a dried film;
c) exposing the dried film to radiation through a mask or a template to form a coated substrate with a dried, pattern-wise exposed film;
d) optionally, baking in a second baking step the coated substrate with a dried, pattern-wise exposed film (e.g., at a temperature from about 50° C. to about 150° C.), in which the exposed portions of the film are crosslinked or cured;
e) developing a portion of the dried, pattern-wise exposed film with a developer (e.g., containing a solvent or a mixture of solvents) to produce a relief image on the substrate (e.g., by contacting the developer with at least some of the unexposed portions of the film), and
f) optionally, rinsing the relief image on the substrate with a solvent or a mixture of solvents, and;
g) optionally, baking the substrate having a relief image (e.g., at a temperature from about 50° C. to about 200° C.) in a third baking step.

In some embodiments, the coating of the substrate can be done by any suitable method including, but not limited to, spin coating, slit coating, spray coating, dip coating and inkjetting. One skilled in the art will know which coating method is appropriate for a given application.

In some embodiments, the first, second, or third baking step can be done using contact or proximity heating on a hotplate at a fixed temperature or by ramping the temperature at a rate of 1-20° C./minute. In some embodiments, the first, second, or third baking step can be done in an oven at a fixed temperature or by ramping the temperature at a rate of 1-20° C./minute either under vacuum or at atmospheric pressure. Irrespective of the baking method used, the first, second, or third baking step can be performed in either a single or multiple steps. Examples of suitable baking means include, but are not limited to, hotplates, infrared lamps, convection ovens, and thermal heating elements on ink jet printing heads. One skilled in the art will know which baking method is appropriate for a given application.

In some embodiments, the exposure step using light, or other radiation (e.g., ultraviolet light, visible light, electron beam radiation, or X-rays), as is suitable for the initiator in the specific composition. The use of i-line (365 nm), h-line (405 nm), or g-line (436 nm) UV light is preferred. In general, the exposure step can result in the curing or crosslinking of the composition, which is not dissolved in the subsequent developing step. One skilled in the art will know which type of high energy radiation is appropriate for a given application.

In some embodiments, after exposure of the film to light or other radiation through a mask or template, unexposed portions are removed by using a developer to form a pattern. Preferred examples of developers include an organic solvent or a mixture of organic solvents. Suitable examples of organic solvents include, but are not limited to, gamma-butyrolactone (GBL), N-methyl-2-pyrrolidone (NMP), dimethylimidazolidinone, N-methylcaprolactam, N-methylpropionamide, N,N-dimethylacetamide (DMAc), dimethyl sulfoxide (DMSO), N,N-dimethylformamide (DMF), N,N-diethylfornamide, diethylacetamide, methyl ethyl ketone (MEK), methyl isobutyl ketone (MIBK), 2-heptanone, cyclopentanone (CP), cyclohexanone, n-butyl acetate (nBA), propylene glycol methyl ether acetate (PGMEA), propylene glycol methyl ether (PGME), ethyl lactate (EL), propyl lactate, 3-methyl-3-methoxybutanol, tetralin, isophorone, ethylene glycol monobutyl ether, diethylene glycol monoethyl ether, diethylene glycol monoethyl ether acetate, diethylene glycol dimethyl ether, diethylene glycol methylethyl ether, triethylene glycol monoethyl ether, dipropylene glycol monomethyl ether, methyl 3-methoxypropionate, ethyl 3-ethoxypropionate, diethyl malonate, ethylene glycol 1,4:3,6-dianhydrosorbitol 2,5-dimethyl ether (2,5-dimethylisosorbide), 1,4:3,6-dianhydrosorbitol 2,5-diethyl ether (2,5-diethylisosorbide) and mixtures thereof. Preferred solvents are gamma-butyrolactone (GBL), cyclopentanone (CP), cyclohexanone, 2,5-dimethyl ether (2,5-dimethylisosorbide), ethyl lactate (EL), n-butyl acetate (nBA) and dimethylsulfoxide (DMSO). These solvents can be used individually or in combination of two or more to improve the image quality.

In some embodiments, the development can be carried out by any suitable method such as spraying the developer described above on the exposed film, immersing the substrate in the developer or applying ultrasonic waves to the substrate while immersing in the developer, spraying the developer while rotating the substrate, or the like. One skilled in the art will know which development method is appropriate for a given application. Development times can range from about 20 seconds to about three minutes. In some embodiments, the development time can range from about 30 seconds to about 2 minutes. In some embodiments, the development time can range from about 45 seconds to about 90 seconds. In some embodiments, multiple development steps can be employed. In some embodiments, two or three development steps can be employed. In some embodiments, two or three development steps are employed where each development step takes from about 25 seconds to about 45 seconds.

In some embodiments, after the development, an optional rinse treatment can be carried out with an organic rinse solvent. Suitable examples of organic rinse solvents include, but are not limited to, alcohols such as isopropyl alcohol, methyl isobutyl carbinol (MIBC), propylene glycol monomethyl ether (PGME), amyl alcohol, esters such as n-butyl acetate (nBA), ethyl lactate (EL) and propylene glycol monomethyl ether acetate (PGMEA), ketones such as cyclopentanone (CP), and mixtures thereof. A rinse solvent can be used to carry out the rinse treatment to remove residues.

In some embodiments, the first baking step temperature is from about 50° C. to about 120° C. In some embodiments, the first baking step temperature is from about 70° C. to about 120° C. In some embodiments, the first baking step temperature is from about 80° C. to about 120° C.

In some embodiments, a second baking step can be incorporated before developing. In some embodiments, the second baking step temperature is from about 40° C. to about 150° C. In some embodiments, the second baking step temperature is from about 50° C. to about 120° C. In some embodiments, the second baking step temperature is from about 50° C. to about 110° C.

In some embodiments, a third baking step can be incorporated after developing. In some embodiments, the third baking step temperature is from about 100° C. to about 200° C. In some embodiments, the third baking step temperature is from about 120° C. to about 180° C.

In some embodiments, the thickness of the film formed on a substrate is preferably from 0.5 µm to 200 µm. The appropriate film thickness employed will be determined by the specific application. One skilled in the art will know which film thickness or range of film thicknesses is appropriate.

Dry Film Structure

Some embodiments of this disclosure relate to a dry film structure that includes a carrier substrate, a protective layer, and a polymeric layer between the carrier substrate and the protective layer. The polymeric layer can include a composition containing components (A), (B), and (C) described above.

In some embodiments, the polyimide-containing compositions described above can be used to prepare the polymeric layer of a dry film. For example, to prepare a dry film structure, a polymeric layer composition is first prepared by mixing at least one polyimide polymer as described earlier, at least one reactive functional compound (RFC), at least one initiator and at least one solvent until a uniform solution is obtained. Optionally, other components such as adhesion promoters, surfactants, plasticizers, nanoparticles, and one or more additional polymers can be used to prepare the polymeric layer composition. The polymeric layer composition thus obtained can then be coated on a carrier substrate to form a polymeric layer.

In some embodiments, the polymeric layer composition used for preparation of a dry film structure of this disclosure can be filtered using a filtration media before it is coated onto a carrier substrate.

In some embodiments, the filtration process is done by using a membrane filter having pore size of 0.2 µm or less. In some embodiments, the material for the membrane filter is preferably polypropylene or Teflon. In some embodiments, only polypropylene filters are used in the filtration process. In such cases, the contact angles of formamide and the surface of filter can range from 30 degrees to 80 degrees as measured in a standard test for measuring the contact angle. In some embodiments, only Teflon filters are used. In such cases, the contact angles of formamide and the surface of the filter can be higher than 80 degree. In some embodiments, multi stage filtration using both polypropylene and Teflon filters are used.

In some embodiments, a hollow fiber membrane filter can be used to filter the polymeric layer composition. Examples of such hollow fiber membrane filters have been described, e.g., in US 20070254243, the content of which is hereby incorporated by reference.

In some embodiments, the polymeric layer in the dry film structure can have a Young's modulus of at least about 0.5 GPa (e.g., at least about 1 GPa, at least about 1.5 GPa, at least about 2 GPa, or at least about 2.5 GPa) to at most about 5 GPa (e.g., at most about 4.5 GPa, at most about 4 GPa, at most about 3.5 GPa, or at most about 3 GPa).

In some embodiments, this disclosure features methods of preparation of a dry film structure. The method includes: (a) coating a carrier substrate with a composition containing at least one polyimide polymer as described earlier, at least one reactive functional compound (RFC), at least one initiator and at least one solvent (b) drying the coated composition to form a first polymeric layer, and (c) applying a protective layer to the first polymeric layer to form a dry film structure.

Some embodiments of this disclosure describe a process for preparation of a dry film structure from a filtered polymeric layer solution. For example, the filtered polymeric layer solution described earlier can be first coated on a carrier substrate to form a first polymeric layer. The carrier substrate typically functions as a mechanical support for the first polymeric layer of the dry film structure during manufacturing, storage and subsequent processing.

In some embodiments, the carrier substrate is a single or multiple layer film, which optionally has undergone treatment to modify the surface of the film that will contact the first polymeric layer of the dry film structure. In some embodiments, one or more layers of a multilayer carrier substrate can contain particles. Examples of particles include, but are not limited to, inorganic particles such as silicon dioxide particles (aggregated silica and the like), calcium carbonate particles, alumina particles, titanium oxide particles, and barium sulfate particles; organic particles such as crosslinked polystyrene particles, acrylic particles, and imide particles; and their mixtures. Without wishing to be bound by theory, it is believed that the particles can improve the adhesion properties of the carrier substrate, and can improve the uniformity of the first polymeric layer coated on the carrier substrate.

In some embodiments, the carrier substrate has excellent optical transparency and is substantially transparent to actinic irradiation used to form a relief pattern in the first polymer layer. In some embodiments, the carrier substrate can possess low surface roughness. The carrier substrate in general should be sufficiently strong and they should be insoluble in the solvent used to form the first polymeric layer. The carrier substrate can be removed from the remainder of the dry film structure (e.g., the first polymeric layer) in subsequent use, or can form part of the final structure of the fabricated device. In situations where the carrier substrate is eventually removed from the final device, such as by peeling, adhesion between the carrier substrate and the first polymeric layer should be weak enough to allow for ease of separation. In such embodiments, the carrier substrate can include a release layer on the surface to be coated by the first polymeric layer to facilitate removal of the carrier substrate. In cases in which the carrier substrate is part of the final device, adhesion should be high to prevent peeling of the carrier substrate.

As specific examples of the carrier substrate, there may be various plastic films such as polyethylene terephthalate (PET), polyethylene naphthalate, polypropylene, polyethylene, cellulose tri-acetate, cellulose di-acetate, poly(metha) acrylic acid alkyl ester, poly(metha)acrylic acid ester copolymer, polyvinylchloride, polyvinyl alcohol, polycarbonate, polystyrene, cellophane, polyvinyl chloride copolymer, polyamide, polyimide, vinyl chloride-vinyl acetate copolymer, polytetrafluoroethylene, polytrifluoroethylene, and the like. In addition, a combination material containing two or more plastic films or two or more polymers can be used. Polyethylene terephthalate (PET) film having excellent optical transparency is particularly preferable. The thickness of the carrier substrate can be in the range of at least about 10 μm (e.g., at least about 15 μm, at least about 20 μm, at least about 30 μm, at least about 40 μm, at least about 50 μm or at least about 60 μm) to at most about 150 μm (e.g., at most about 140 μm, at most about 120 μm, at most about 100 μm, at most about 90 μm, at most about 80 μm, or at most about 70 μm). The Young's modulus of the carrier substrate can be in the range of at least about 100 MPa (e.g., at least about 150 MPa, at least about 200 MPa, or at least about 250 MPa) to at most about 500 MPa (e.g., at most about 450 MPa, at most about 400 MPa, or at most about 350 MPa).

The carrier substrate can be used with or without corona treatment. Corona is ionized air created by discharging high frequency high voltage energy across a metal or insulated electrode. This electrode is positioned over a grounded roll. The corona treatment of films can optimize surfaces for adhesion by removing surface contaminants, creating bonding sites and raising the surface energy. In some embodiments, corona treatment can be done during winding of the carrier substrate film to form a roll by passing the film through a corona process. This produces pretreated corona film. Such corona treated carrier substrate films are commercially available. Another option is "online corona treatment" where the carrier substrate film is passed through a corona chamber just before coating of the first polymeric layer composition onto the carrier substrate. On line corona treatment of carrier substrates can improve print quality, eliminates pinholing in coating, and increases dry film structure productivity.

The coating method to form the first polymeric layer of the dry film structure is not particularly limited. For example, methods such as spray coating, roll coating, rotation coating, slit coating, compression coating, curtain coating, die coating, wire bar coating, and knife coating can be used to form the first polymeric layer. The drying temperature used to form the first polymeric layer can vary according to the components, the organic solvent, and the content ratio. In some embodiments, drying is carried out at a temperature of at least about 60° C. (e.g., at least about 65° C., at least about 70° C. or at least about 75° C.) to at most about 120° C. (e.g., at most about 105° C., at most about 90° C. or at most about 85° C.) for at least about 30 seconds (e.g., at least about 1 minute, at least about 2 minutes, at least about 4 minutes or at least about 6 minutes) to at most about 15 minutes (e.g., at most about 12 minutes, at most about 10 minutes, or at most about 8 minutes). An example of a drying means is a convection oven using hot air, but any suitable heating means can be employed.

The thickness of the first polymeric layer of the dry film structure of the present disclosure is not particularly limited. The thickness is preferably at least about 2 μm (e.g., at least about 5 μm, at least about 10 μm, at least about 20 μm, at least about 25 μm, at least about 30 μm, at least about 35 μm or at least about 40 μm) and/or at most about 100 μm (e.g., at most about 90 μm, at most about 80 μm, at most about 70 μm, at most about 60 μm, at most about 50 μm or at most about 45 μm). In some embodiments, the first polymeric layer can have a relatively small thickness. In such embodiments, the first polymeric layer can have a thickness of at most about 10 μm (e.g., at most about 5 μm, at most about 4 μm, or at most about 3 μm).

In some embodiments, melt viscosity and melting point can be important thermal properties of the above described first polymeric layer. Both of these properties can be critical for effective lamination of the dry film structure onto a substrate.

In some embodiments, the dry film structure contains a first polymeric layer having a melt viscosity of at least about 10 poise (e.g., at least about 20 poise, at least about 30 poise, at least about 40 poise or at least about 50 poise) and/or at most 150 poise (e.g., at most about 140 poise, at most about 130 poise, at most about 120 poise, at most about 110 poise, at most about 100 poise or at most about 90 poise) at a temperature from about 60° C. to about 140° C. Without wishing to be bound by theory, it is believed that, when melt viscosity of the first polymeric layer is too low, over-flowing of the first polymeric layer can occur during lamination. This results in inconsistent film thickness of the laminated film and contamination of the backside of substrate. When the melt viscosity is too high, polymer flow can be unusually slow which results in voids and air-bubbles in the layer thus formed. Moreover, if the carrier substrate is patterned, low polymer flow can cause incomplete and improper filling of the patterns.

In some embodiments, the first polymeric layer has a melting point of at least about 60° C. (e.g., at least 65° C., at least about 70° C., at least about 75° C., or at least about 80° C.) and/or at most about 140° C. (e.g. at most about 135° C., at most about 130° C., at most about 125° C., or at most about 120° C.). Without wishing to be bound by theory, it is believed that, when the melting point of the first polymeric layer is too low, formation of a dry film can be hindered to such a degree that the formation of the dry film stack, typically by a continuous process, is hindered. When the melting point is too high, a high temperature is needed during lamination of the first polymeric layer and the carrier substrate and can cause the carrier substrate to be melted, thereby ruining the dry film stack. In addition, when a first polymeric layer with a high melting point is used in a lower temperature lamination process, the first polymeric layer can have poor adhesion with the carrier layer.

In some embodiments, the dry film structure includes a protective layer (e.g., a protective film or a protective cover sheet) so that the first polymeric layer is disposed between the protective layer and the carrier substrate. The protective layer can protect the first polymeric layer during transit and storage, and keeping the tacky first polymeric layer from sticking to itself. In some embodiments, the protective layer is a single or multiple layer film which optionally has undergone treatment to modify the surface of the film that will contact the first polymeric layer of the dry film structure. The protective layer can be made from polyethylene, polypropylene, or any other suitable polymer. In some embodiments, adhesion of the protective layer to the first polymeric layer is less than that of the carrier substrate to the first polymeric layer. This allows for easy separation of the protective layer from the first polymeric layer without also separating the first polymeric layer from the carrier substrate. The protective layer can be laminated to the first polymeric layer by a roll compression method.

In some embodiments, the protective layer can have a Young's modulus in the range of at least about 100 MPa (e.g., at least about 150 MPa, at least about 200 MPa, or at least about 250 MPa) to at most about 500 MPa (e.g., at most about 450 MPa, at most about 400 MPa, or at most about 350 MPa).

In general, the dry film structure described herein can be used to laminate the first polymeric layer to a substrate (e.g., an electronic substrate). In some embodiments, the first polymeric layer of the dry film structure can be laminated to any type of substrates (e.g., electronic substrates) using a differential pressure laminator where vacuum, heat, and pressure are combined for voidless lamination. Examples of suitable electronic substrates include a silicon substrate, a copper substrate, an aluminum substrate, a silicon oxide substrate, a silicon nitride substrate, a glass substrate, an organic laminate substrate, or a dielectric material substrate. For example, the protective layer of the dry film structure can be peeled off, and the remainder of the structure (e.g., a first polymeric layer on a carrier substrate) can then be cut to the substrate size. As another example, the dry film structure can first be cut to the substrate size and then the protective layer can be peeled off to laminate the first polymeric layer onto a substrate. In some embodiments, these substrates, pre-laminated either manually or with the assistance of currently available dispensing equipment, are placed on the slide mounted platen or positioned in a chamber. Substrates varying in thickness and geometry can be intermixed to increase throughput. The substrate can then be exposed to a vacuum dwell for a time determined by an integral precision digital timer. Following this period, a preheated silicone rubber diaphragm can descend onto the work piece. This action can close the small gap below the spring-mounted platen assembly and provides direct thermal contact with the lower heat platen. The temperatures of both the upper and lower heated platens can be controlled independently by integral temperature controllers. Differential pressure laminator generally permits the addition of positive pressure above the diaphragm, increasing the effective lamination pressure dramatically. The pressure dwell period can be adjusted with a timer identical to that employed in the vacuum dwell. Upon completion of a cycle, the drawer mechanism can be retracted and the laminated substrate can be removed for further processing.

In some embodiments, the first polymeric layer can be laminated to a substrate through a vacuum lamination at 60° C. to 140° C. after pre-laminating of the first polymeric layer of the dry film structure with a plane compression method or a hot roll compression method. When the hot roll lamination is employed, the dry film structure can be placed into a hot roll laminator, the protective layer can be peeled away from the first polymeric layer/carrier substrate, and the first polymeric layer can be brought into contact with and laminated to a substrate using rollers with heat and pressure.

In some embodiments, the lamination temperature used in the lamination process described above is at least about 50° C. (e.g., at least about 70° C., at least about 80° C., at least about 90° C., or at least about 100° C.) to at most about 220° C. (e.g., at most about 190° C., at most about 170° C., at most about 130° C., or at most about 110° C.). The pressure used in the lamination process described above is at least about 1.5 psi (e.g., at least about 3 psi, at least about 5 psi, at least about 10 psi, at least about 15 psi, or at least about 20 psi) to preferably at most about 70 psi (e.g., at most about 60 psi, at most about 50 psi, at most about 40 psi, or at most about 30 psi). The vacuum used in the lamination process described above can be at least about 0.2 torr to at most about 5 torr. The speed of the roller used in the lamination process described above can be at least about 1 cm/min (e.g., at least about 5 cm/min, at least about 10 cm/min, at least about 25 cm/min, or at least about 50 cm/min) to at most about 600 cm/min (e.g., at most about 500 cm/min, at most about 400 cm/min, at most about 300 cm/min at most about 200 cm/min, or at most about 100 cm/min).

In some embodiments, this disclosure features a process of forming a laminate. The process can include (a) removing the protective layer from the dry film structure described herein; and (b) applying the film structure obtained in step (a) onto an electronic substrate to form a laminate. In some embodiments, the process can further include converting the first polymeric layer into a patterned layer. The conversion can include exposing the first polymeric layer in the laminate to actinic radiation. In such embodiments, the conversion can further include removing the carrier substrate before or after exposing the first polymeric layer. After the first polymeric layer is exposed to actinic radiation, the conversion can further include developing the exposed first polymeric layer to form a patterned layer having a relief pattern.

In some embodiments, the laminated first polymeric layer on an electronic substrate is exposed through a desired patterned photomask such that the exposed areas in the first polymeric layer is crosslinked. Examples of active energy beams used for exposure include electron beams, ultraviolet light and X-ray, with ultraviolet light being preferable. As a light source, it is possible to use a low-pressure mercury lamp, high-pressure mercury lamp, extra-high-pressure mercury lamp, halogen lamp, etc. The exposure dose is typically from about 100 mJ/cm$^2$ to about 1,000 mJ/cm$^2$.

The carrier substrate can be removed by peeling before or after the exposure.

After the exposure, the first polymeric layer of the dry film structure can be heat treated to at least about 50° C. (e.g., at least about 55° C., at least about 60° C., or at least about 65° C.). to at most about 100° C. (e.g., at most about 95° C., or at most about 90° C., at most about 85° C., at most about 80° C., at most about 75° C., or at most about 70° C.) for at least about 60 seconds (e.g., at least about 65 seconds, or at least about 70 seconds) to at most about 90 seconds (e.g., at most about 85 minutes, or at most about 80 seconds). The heat treatment is usually accomplished by use of a hot plate or oven.

After the exposure, the first polymeric layer of the dry film structure can be developed to remove unexposed portions by using a developer. Development can be carried out by, for example, an immersion method or spraying method. Microholes and fine lines can be generated in the photosensitive first polymeric layer on the laminated substrate after development.

Examples of developers for developing the first polymeric layer include an organic solvent or a mixture of organic solvents. Suitable examples of organic solvents include, but are not limited to, gamma-butyrolactone (GBL), N-methyl-2-pyrrolidone (NMP), N-ethyl-2-pyrrolidone, N-butyl-2-pyrrolidone, N-formylmorpholine, dimethylimidazolidinone, N-methylcaprolactam, N-methylpropionamide, N,N-dimethylacetamide (DMAc), dimethyl sulfoxide (DMSO), N,N-dimethylformamide (DMF), N,N-diethylformamide, diethylacetamide, methyl ethyl ketone (MEK), methyl isobutyl ketone (MIBK), 2-heptanone, cyclopentanone (CP), cyclohexanone, n-butyl acetate (nBA), propylene glycol methyl ether acetate (PGMEA), propylene glycol methyl ether (PGME), ethyl lactate (EL), propyl lactate, 3-methyl-3-methoxybutanol, tetralin, isophorone, ethylene glycol monobutyl ether, diethylene glycol monoethyl ether, diethylene glycol monoethyl ether acetate, diethylene glycol dimethyl ether, diethylene glycol methylethyl ether, triethylene glycol monoethyl ether, dipropylene glycol monomethyl ether, methyl 3-methoxypropionate, ethyl 3-ethoxypropionate, diethyl malonate, ethylene glycol 1,4:3,6-dianhydrosorbitol 2,5-dimethyl ether (2,5-dimethylisosorbide), 1,4:3,6-dianhydrosorbitol 2,5-diethyl ether (2,5-diethylisosorbide) and mixtures thereof. Preferred solvents are gamma-butyrolactone (GBL), cyclopentanone (CP), cyclohexanone, 2,5-dimethyl ether (2,5-dimethylisosorbide), ethyl lactate (EL), n-butyl acetate (nBA) and dimethylsulfoxide (DMSO). These solvents can be used individually or in combination of two or more to improve the image quality.

In some embodiments, the developer and the polyimide polymer in the first polymeric layer can have a relative energy difference (RED) of at most about 3 (e.g., at most about 2.5, at most about 2, at most about 1.5, or at most about 1) and/or at least about 0.1 (e.g., at least about 0.2, at least about 0.5, at least about 0.7, or at least about 1).

In some embodiments, after the development, an optional rinse treatment can be carried out with an organic rinse solvent. Suitable examples of organic rinse solvents include, but are not limited to, alcohols such as isopropyl alcohol, methyl isobutyl carbinol (MIBC), propylene glycol monomethyl ether (PGME), and amyl alcohol; esters such as n-butyl acetate (nBA), ethyl lactate (EL) and propylene glycol monomethyl ether acetate (PGMEA); ketones such as cyclopentanone (CP); and mixtures thereof. A rinse solvent can be used to carry out the rinse treatment to remove residues.

In some embodiments, after the development step or the optional rinse treatment step, an optional baking step can be carried out at a temperature ranging from at least about 120° C. (e.g., at least about 130° C., at least about 140° C., at least about 150° C., at least about 160° C., at least about 170° C., at least about 180° C.) to at most about 250° C. (e.g., at most about 240° C., at most about 230° C., at most about 220° C., at most about 210° C., at most about 200° C. or at most about 190° C.). The baking time is at least about 5 minutes (e.g., at least about 10 minutes, at least about 20 minutes, at least about 30 minutes, at least about 40 minutes, at least about 50 minutes, or at least about 60 minutes) and/or at most about 5 hours (e.g., at most about 4 hours, at most about 3 hours, at most about 2 hours, or at most about 1.5 hours). This baking step can remove residual solvent from the remaining first polymeric layer and can further cure the remaining first polymeric layer. Curing can be done in air or preferably, under a blanket of nitrogen and may be carried out by any suitable heating means.

In embodiments where the first polymeric layer contains a thermal initiator, a curing step can be done after the lamination of the first polymeric layer to the electronic substrate and before or after removal of the carrier substrate.

In some embodiments, the resulting baked first polymeric layer after the baking step has a glass transition temperature of at least about 180° C. (e.g., at least about 190° C., at least about 200° C. or at least about 210° C.). In some embodiments, the resulting baked first polymeric layer after the baking step has a glass transition of at most about 320° C. (e.g. at most about 310° C., at most about 300° C. or at most about 290° C.). As used herein, the glass transition temperature of the first polymeric layer is defined as the first inflection point on a thermo-mechanical analyzer curve plotting dimension change (μ) vs temperature.

In some embodiments, a high glass transition temperature for the baked first polymeric layer can be desirable to prevent film mobility during subsequent processing steps of device manufacture and subsequent device use for longer device life. Some manufacturing processing steps such as soldering require elevated temperatures. High glass transition temperature for the baked first polymeric layer can help maintain mechanical integrity of the resulting devices.

In general, the processes described above can be used to form an article to be used in a semiconductor device. Examples of such articles include a semiconductor substrate, a flexible film for electronics, a wire isolation, a wire coating, a wire enamel, or an inked substrate. Examples of semiconductor devices that can be made from such articles include an integrated circuit, a light emitting diode, a solar cell, and a transistor.

In some embodiments, the processes described above result in an article that includes an electronic substrate and a patterned layer (e.g., containing a relief pattern) laminated onto the electronic substrate, in which the patterned layer includes at least one polyimide polymer. Without wishing to be bound by theory, it is believed that the patterned layer thus formed can have a relatively small thickness with a relatively high resolution. For example, the patterned layer can have a thickness of at most about 5 microns (e.g., at most about 4 microns or at most about 3 microns) and include at least one element having a feature size of at most about 2 microns.

In some embodiments, the patterned layer can have a Young's modulus of at least about 1 GPa (e.g., at least about 2 GPa, at least about 3 GPa, at least about 4 GPa, or at least about 5 GPa) to at most about 20 GPa (e.g., at most about 18 GPa, at most about 16 GPa, at most about 14 GPa, at most about 12 GPa, or at most about 10 GPa). In some embodiments, the patterned layer can have a Young's modulus that is about 200% to about 300% as high as the Young's modulus of the first polymeric layer of the dry film structure.

In some embodiments, the dry film structure described above can further include a second polymeric layer containing at least one water soluble polymer. As defined herein, a "water-soluble" polymer refers to a polymer having a solubility of at least 5% by weight in water at 25° C. Examples of suitable water soluble polymer can be selected from a group consisting of poly(vinyl alcohol), poly(vinyl pyrrolidone), poly(acrylic acid) and the salts thereof, poly(methacrylic acid) and the salts thereof, poly(acrylamide) and the salts thereof, poly(methacrylamide) and the salts thereof, poly(N-isopropylacrylamide) and the salts thereof, poly (2-oxazoline), poly(ethylene oxide), poly(propylene oxide), hydroxyethyl cellulose, hydroxypropyl cellulose, starch, polysaccharides, dextran, cyclodextran, and partially hydrolyzed polyvinyl acetate.

In some embodiments, the second polymeric layer can be between the first polymeric layer and the carrier substrate in the dry film structure. In such embodiments, when the dry film structure is laminated onto an electronic substrate and the carrier substrate is removed, the laminate thus formed includes the electronic substrate, the first polymeric layer (which can be photosensitive), and the second water soluble polymeric layer in the above order. In such embodiments, the second polymeric layer can improve the post exposure delay stability of the first polymeric layer by serving as a protecting layer. In such embodiments, the second polymeric layer can be removed by using water after exposure of the laminate to the actinic radiation and before development.

In some embodiments, the second polymeric layer can be between the first polymeric layer and the protective layer in the dry film structure. In such embodiments, when the dry film structure is laminated onto an electronic substrate and the carrier substrate is removed, the laminate thus formed includes the electronic substrate, the second water soluble polymeric layer, and the first polymeric layer (which can be photosensitive) in the above order. In such embodiments, the second polymeric layer can serve as a protecting layer of the electronic substrate when the electronic substrate is sensitive to an organic developer (e.g., when the electronic substrate is an organic substrate). In such embodiments, after development, part of the water soluble second polymeric layer (i.e., that under the unexposed/developed portion of the first polymeric layer) can be removed by using water, and the rest of second polymeric layer (i.e., that under the exposed/undeveloped portion of the first polymeric layer) can remain in the device thus formed.

The contents of all publications cited herein (e.g., patents, patent application publications, and articles) are hereby incorporated by reference in their entirety.

The following examples are provided to illustrate the principles and practice of the present disclosure more clearly. It should be understood that the present disclosure is not limited to the examples described.

EXAMPLES

Synthesis Example 1 (Diamine-1)

4,4'-but-1-ene-3,3-diyldianiline

To a 3-neck round bottom flask equipped with a mechanical stirrer and a reflux condenser is added 13.0 grams of aniline hydrochloride, 7.1 grams of methyl vinyl ketone, 120 grams of diglyme (diethylene glycol dimethyl ether) and 0.2 grams of zinc chloride as a catalyst. The mixture is stirred at 0° C. for 2 hours. The mixture is held at 170° C. for 8 hours and then is cooled to room temperature. The cold solution is neutralized with a 25 wt % aqueous sodium carbonate solution. The neutralized solution is precipitated into 1 L distilled water. The solid is isolated by filtration and then the filtered cake is further washed with 100 ml of distilled water. The crude solid is purified by recrystallization from aqueous ethanol.

Structure of Diamine-1

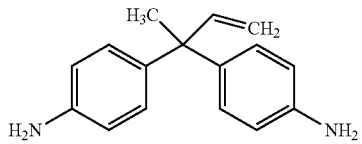

Synthesis Example 2 (Diamine-2)

4,4'-(pent-4-ene-2,2-diyl)dianiline

To a 3-neck round bottom flask equipped with a mechanical stirrer and a reflux condenser is added 13.0 grams of aniline hydrochloride, 8.4 grams of 4-penten-2-one, 120 grams of diglyme (diethylene glycol dimethyl ether), and 0.2 grams of zinc chloride as a catalyst. The mixture is stirred at 0° C. for 2 hours. The mixture is held at 170° C. for 8 hours and then is cooled to room temperature. The cold solution is neutralized with a 25 wt % aqueous sodium carbonate solution. The neutralized solution is precipitated into 1 L distilled water. The solid is isolated by filtration and then the filtered cake is further washed with 100 ml distilled water. The crude solid is purified by recrystallization from aqueous ethanol.

Structure of Diamine-2

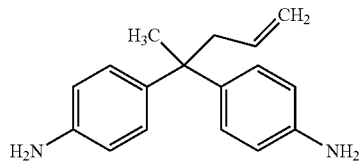

Synthesis Example 3 (Poly-1)

Example of Polymer With End-Capping Group

The polymerization reaction is carried out in a one liter three-neck, jacketed, round bottomed flask equipped with a mechanical agitator, a thermocouple and a nitrogen inlet to keep positive nitrogen pressure throughout the reaction. The flask is charged with 59.07 grams of benzophenone-3,3',4,4'-tetracarboxylic dianhydride (BTDA) and 200 grams of anhydrous NMP. The contents are agitated at 18-20° C. 40.95 grams of 1-(4-aminophenyl)-1,3,3-trimethylindan-5-amine (DAPI), and 9.15 grams of 4,4'-but-1-ene-3,3-diyl-dianiline are dissolved in 100 grams of dry NMP in a bottle. The diamine solution is added to the flask by pump for 1 hour at room temperature. The mixture is warmed to 60° C. and agitated for 3 hours.

To endcap the polyamic acid formed above, 11.13 grams of 4-methacryloxyethyltrimellitic acid anhydride (META) is charged to the flask. The mixture is agitated at 60° C. for 3 hours.

To carry out the imidization reaction, 10.85 grams of acetic anhydride and 4.15 grams of pyridine are charged to the flask. The reaction mixture is warmed to 100° C. and agitated for 12 hours. The solution is cooled to room temperature and is added dropwise to 4 liters of vigorously stirred de-ionized water to precipitate the polymer. The polymer is collected by filtration and washed with one liter of de-ionized water. The cake is re-slurried with one liter of methanol and filtered. The wet cake is dried in air for 12 hours and then the polymer is dried under vacuum at 70° C. for 12 hours. The molecular weight of the resultant polyimide polymer (Poly-1) is measured by GPC.

Synthesis Example 4 (Poly-2)

Example of Polymer Without End-Capping Group

The polymerization reaction is performed in a one liter three-neck, jacketed, round bottomed flask equipped with a mechanical agitator, a thermocouple and a nitrogen inlet to keep positive nitrogen pressure throughout the reaction. The flask is charged with 59.07 grams of benzophenone-3,3',4,4'-tetracarboxylic dianhydride (BTDA) and 200 grams of anhydrous NMP. The contents are agitated at 18-20° C. 40.95 grams of 1-(4-aminophenyl)-1,3,3-trimethylindan-5- amine (DAPI), and 9.15 grams of 4,4'-but-1-ene-3,3-diyl-dianline are dissolved in 100 grams of dry NMP in a bottle. The diamine solution is added to the flask by pump for 1 hour at room temperature. The mixture is warmed to 60° C. and agitated for 3 hours.

To carry out the imidization reaction, 21.70 grams of acetic anhydride and 4.15 grams of pyridine are charged to the flask. The reaction mixture is warmed to 100° C. and agitated for 12 hours. The solution is cooled to room temperature and is added dropwise to 4 liters of vigorously stirred de-ionized water to precipitate the polymer. The polymer is collected by filtration and washed with one liter of de-ionized water. The cake is re-slurried with one liter of methanol and filtered. The wet cake is dried in air for 12 hours and then the polymer is dried under vacuum at 70° C. for 12 hours. The molecular weight of the resultant polyimide polymer (Poly-2) is measured by GPC.

Synthesis Example 5 (Poly-3)

The polymerization reaction is carried out in a one liter three-neck, jacketed, round bottomed flask equipped with a mechanical agitator, a thermocouple and a nitrogen inlet to keep positive nitrogen pressure throughout the reaction. The flask is charged with 50.91 grams of benzophenone-3,3',4,4'-tetracarboxylic dianhydride (BTDA) and 17.55 grams of 2,2'-bis-(3,4-dicarboxyphenyl)-hexafluoropropane dianhydride (6FDA) and 200 grams of anhydrous NMP. The contents are agitated at 18-20° C. 39.96 grams of 1-(4-aminophenyl)-1,3,3-trimethylindan-5-amine (DAPI) and 11.98 grams of 4,4'-trans-stilbene diamine are dissolved in 180 grams of dry NMP in a bottle. The diamine solution is added to the flask by pump for 1 hour at room temperature. The mixture was warmed to 60° C. and agitated for 3 hours.

To endcap the polyamic acid formed above, 6.42 grams of 4-methacryloxyethyltrimellitic acid anhydride (META) is charged to the flask. The mixture is agitated at 60° C. for 3 hours.

To carry out the imidization reaction, 40.2 grams of acetic anhydride and 7.91 grams of pyridine are charged to the flask. The reaction mixture is warmed to 100° C. and agitated for 12 hours. The solution is cooled to room temperature and is added dropwise to 4 liters of vigorously stirred de-ionized water to precipitate the polymer. The polymer is collected by filtration and washed with one liter of de-ionized water. The cake is re-slurried with one liter of methanol and filtered. The wet cake is dried in air for 12 hours and then the polymer is dried under vacuum at 70° C. for 12 hours. The molecular weight of the resultant polyimide polymer (Poly-3) is measured by GPC.

Synthesis Example 6 (Poly-4)

The polymerization reaction is carried out in a one liter three-neck, jacketed round bottomed flask equipped with a mechanical agitator, a thermocouple and a nitrogen inlet to keep positive nitrogen pressure throughout the reaction. The flask is charged with 50.91 grams of benzophenone-3,3',4,4'-tetracarboxylic dianhydride (BTDA), 8.78 grams of 2,2'-bis-(3,4-dicarboxyphenyl)-hexafluoropropane dianhydride (6FDA), 6.05 grams of 4,4'-oxydiphthalic anhydride (ODPA) and 200 grams of anhydrous NMP. The contents are agitated at 18-20° C. 39.96 grams of 1-(4-aminophenyl)-1,3,3-trimethylindan-5-amine (DAPI), 7.59 grams of 4,4'-(1,1-dimethyl-3-methylene-1,3-propanediyl)bisbenzamine, and 7.59 grams of 4,4'-(1,3,3-trimethyl-1-propene-1,3-diyl) bisbenzamine are dissolved in 220 grams of dry NMP in a bottle. The diamine solution is added to the flask by pump for 1 hour at room temperature. The mixture was warmed to 60° C. and agitated for 3 hours.

To endcap the polyamic acid formed above, 6.42 grams of 4-methacryloxyethyltrimellitic acid anhydride (META) is charged to the flask. The mixture is agitated at 60° C. for 3 hours.

To carry out the imidization reaction, 40.2 grams of acetic anhydride and 7.91 grams of pyridine are charged to the flask. The reaction mixture is warmed to 100° C. and agitated for 12 hours. The solution is cooled to room temperature and is added dropwise to 4 liters of vigorously stirred de-ionized water to precipitate the polymer. The polymer is collected by filtration and washed with one liter of de-ionized water. The cake is re-slurried with one liter of methanol and filtered. The wet cake is dried in air for 12 hours and then the polymer is dried under vacuum at 70° C. for 12 hours. The molecular weight of the resultant polyimide polymer (Poly-3) is measured by GPC.

Composition Example 1

To a 3-neck round bottom flask equipped with a mechanical stirrer are added 60 grams of GBL, 10 grams of the polymer Poly-1 obtained in Synthesis Example 3, 0.6 grams of a 0.5 wt % solution of PolyFox 6320 (available from OMNOVA Solutions) in GBL, 0.3 grams of 3-ethoxysilyl propyl ethoxycarbamate, 0.4 grams of NCI-831 (trade name, available from ADEKA corporation) and 4.0 grams of tetraethylene glycol dimethacrylate. The above composition is mechanically stirred for 30 hours and then filtered by using a 0.2 μm filter (Ultradyne from Meissner Filtration Product, Inc., cat. no. CFTM 0.2-44B1).

Process Example 1

The photosensitive composition from Composition Example 1 is spin coated on a silicon wafer to form a coating with a thickness of about 10 microns. The coated wafer is baked at 105° C. for 3 minutes. The photosensitive polyimide film is exposed with a broadband UV exposure tool (Carl Süss MA-56) through a mask having a desired pattern for exposure.

After the exposure, unexposed portions are removed by using a mixture of 65 wt % GBL and 35 wt % cyclopentanone as a developer, followed by rinsing the developed film with PGMEA to form a pattern. After pattern formation, the developed film is heated at 50° C. for 3 minutes. The resulting film is checked by optical microscope for film defects. The film is cured under $N_2$ atmosphere in a convection oven at 200° C. for 1 hour.

Composition Example 2

The composition of this example is made by the same method as described in Composition Example 1 except the polyimide Poly-2 from Synthesis Example 4, instead of Poly-1 from Synthesis Example 3, is used.

Process Example 2

The photosensitive composition prepared in Composition Example 2 is spin coated on a silicon wafer to form a coating with a thickness of 10 microns. The coated wafer is baked at 105° C. for 3 minutes. The photosensitive polyimide film is exposed with a broadband UV exposure tool (Carl Süss MA-56) through a mask having a desired pattern for exposure.

After the exposure, unexposed portions are removed by using a mixture of 65 wt % GBL and 35 wt % cyclopentanone as a developer, followed by rinsing the developed film with PGMEA to form a pattern. After pattern formation, the developed film is heated at 50° C. for 3 minutes. The resulting film is checked by optical microscope for film defects. The film is cured under N$_2$ atmosphere in a convection oven at 200° C. for 1 hour.

Composition Example 3

To a 3-neck round bottom flask equipped with a mechanical stirrer are added 45.0 grams of GBL, 10.0 grams of dimethyl sulfoxide (DMSO), 10.0 grams of the polymer obtained in Synthesis Example 5 (Poly-3), 0.5 grams of a 0.5 wt % solution of PolyFox 6320 (available from OMNOVA Solutions) in GBL, 0.4 grams of 3-glycidoxypropyl trimethoxy silane, 0.5 grams of diphenyl(2,4,6-trimethylbenzoyl)phosphine oxide and 3.75 grams of pentaerylthritol triacrylate. The above composition is mechanically stirred for 30 hours and then filtered by using a 0.2 μm filter (Ultradyne from Meissner Filtration Product, Inc., cat. no. CFTM 0.2-44B1).

Dry Film Example DF-1

The filtered, photosensitive solution of Composition Example 3 is applied onto a polyethylene naphthalate film having a thickness of 25 μm used as a carrier substrate and is dried at 230° F. to obtain a polymeric layer with a thickness of approximately 10.0 microns. On this polymeric layer, a polyethylene film is laid over by a roll compression to form a protective layer.

Lamination of Dry Film Example L-1

After the removal of the protective layer by peeling, the polymeric layer of the dry film DF-1 (6"×6") is placed against a 4" Wafernet copper coated wafer. The polymeric layer is laminated onto the Cu coated wafer by vacuum lamination at 105° C. followed by being subjected to a pressure of 30 psi for 90 seconds. The lamination process is done by using a DPL-24A Differential Pressure Laminator manufactured by OPTEK, NJ. A film thickness of resulting photosensitive polymeric layer is 10.0 microns.

Lithographic Evaluation of Laminated DF-1

The carrier substrate of the copper wafer laminated by DF-1 in Example L-1 is removed. The photosensitive polymeric layer is then exposed to actinic light utilizing an i-line stepper in a patterned exposure array, which incrementally increases exposure energy 25 mJ/cm$^2$ with a starting exposure energy of 100 mJ/cm$^2$. The exposed film is then heated at 50° C. for 3 minutes, and developed using two 30-second puddles with a solution containing 70 wt % GBL and 30 wt % cyclopentanone. The film is then washed with PGMEA. A relief pattern is obtained.

Composition Example 4

To a 3-neck round bottom flask equipped with a mechanical stirrer are added 40.0 grams of GBL, 10.0 grams of cyclopentanone, 10.0 grams of cyclohexanone, 10.0 grams of the polymer obtained in Synthesis Example 6 (Poly-4), 0.25 grams of a 0.5% solution of PolyFox 6320 (available from OMNOVA Solutions) in GBL, 0.35 grams of 3-triethoxy silyl propyl ethyl carbamate, 0.2 grams of diphenyl (2,4,6-trimethylbenzoyl)phosphine oxide, 0.2 grams of NCI-831 (trade name, available from ADEKA corporation), 2.0 grams of tetraethylene glycol acrylate and 2.0 grams of pentaerylthritol triacrylate. The above composition is mechanically stirred for 36 hours and then filtered by using a 0.2 μm filter (Ultradyne from Meissner Filtration Product, Inc., cat. no. CFTM 0.2-44B1).

Dry Film Example DF-2

The filtered, photosensitive solution of Composition Example 4 is applied onto a polyethylene naphthalate film having a thickness of 25 μm used as a carrier substrate and is dried at 220° F. to obtain a polymeric layer with a thickness of approximately 11.0 microns. On this polymeric layer, a polyethylene film is laid over by a roll compression to form a protective layer.

Lamination of Dry Film Example L-2

After the removal of the protective layer by peeling, the polymeric layer of the dry film DF-2 (6"×6") is placed against a 4" Wafernet copper coated wafer. The polymeric layer is laminated onto the Cu coated wafer by vacuum lamination at 115° C. followed by being subjected to a pressure of 25 psi for 120 seconds. The lamination process is done by using a DPL-24A Differential Pressure Laminator manufactured by OPTEK, NJ. A film thickness of resulting photosensitive polymeric layer is 11.0 microns.

Lithographic Evaluation of Laminated DF-1

The carrier substrate of the copper wafer laminated by DF-2 in Example L-2 is removed. The photosensitive polymeric layer is then exposed to actinic light utilizing an i-line stepper in a patterned exposure array, which incrementally increases exposure energy 25 mJ/cm$^2$ with a starting exposure energy of 100 mJ/cm$^2$. The exposed film is then heated at 50° C. for 3 minutes, and developed using two 30-second puddles with a solution containing 60 wt % GBL and 40 wt % cyclopentanone. The film is then washed with PGMEA. A relief pattern is obtained. The film is then heated at 190° C. for 90 minutes.

What is claimed is:
1. A polyimide polymer, comprising the reaction product of components (a), (b), (c), and optionally (d), wherein components (a), (b), (c), and (d) are:
(a) at least one diamine selected from the group consisting of a diamine of Structure (Ia) and a diamine of Structure (Ib):

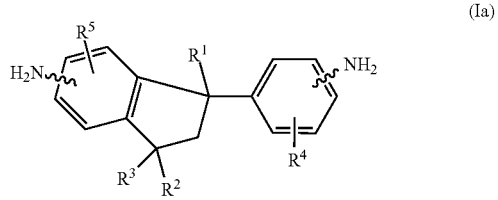

49

-continued

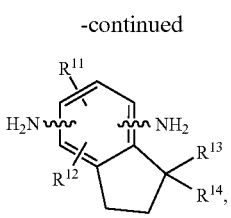

(Ib)

(b) at least one diamine of Structure (IIa):

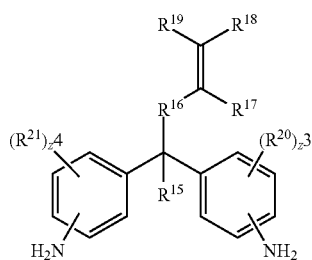

Structure (IIa)

wherein
each of $z^3$ and $z^4$, independently, is an integer ranging from 0 to 4;
$R^{15}$ is a hydrogen atom, a substituted or unsubstituted linear $C_1$-$C_4$ alkyl group, a substituted or unsubstituted branched $C_3$-$C_4$ alkyl group, a substituted or unsubstituted $C_5$-$C_8$ cycloalkyl group, a substituted or unsubstituted phenyl group, or —$R^{22}$—C($R^{23}$)=C($R^{24}R^{25}$), in which $R^{22}$ is —(CH$_2$)$_z^6$—; each of $R^{23}$, $R^{24}$ and $R^{25}$, independently, is a hydrogen atom, a substituted or unsubstituted linear $C_1$-$C_4$ alkyl group, a substituted or unsubstituted branched $C_3$-$C_4$ alkyl group, a substituted or unsubstituted $C_5$-$C_8$ cycloalkyl group, or a substituted or unsubstituted phenyl group; and $z^6$ is an integer from 0 to 4;
$R^{16}$ is —(CH$_2$)$_z^5$—, in which $z^5$ is an integer from 1 to 4;
each of $R^{17}$, $R^{18}$, and $R^{19}$, independently, is a hydrogen atom, a substituted or unsubstituted linear $C_1$-$C_4$ alkyl group, a substituted or unsubstituted branched $C_3$-$C_4$ alkyl group, a substituted or unsubstituted $C_5$-$C_8$ cycloalkyl group, a substituted or unsubstituted phenyl group; and
each $R^{20}$ and each $R^{21}$, independently, is a hydrogen atom, a substituted or unsubstituted linear $C_1$-$C_4$ alkyl group, a substituted or unsubstituted branched $C_3$-$C_4$ alkyl group, a substituted or unsubstituted $C_5$-$C_8$ cycloalkyl group or a halogen atom,
(c) at least one tetracarboxylic acid dianhydride, and optionally,
(d) at least one compound containing a first functional group reactive with an amine or an anhydride and at least one second functional group selected from the group consisting of a substituted or unsubstituted alkenyl group and a substituted or unsubstituted alkynyl group, wherein the first functional group reactive to an amine is selected from the group consisting of an anhydride group, an acid halide group, an epoxy group, and an isocyanate group and the first functional group reactive to an anhydride is selected from the group consisting of an amino group, a hydroxyl group, and a thiol group,

50 wherein each of $R^1$, $R^2$, $R^3$, $R^4$, $R^5$, $R^{11}$, $R^{12}$, $R^{13}$, and $R^{14}$, independently, is H, a substituted or unsubstituted linear $C_1$-$C_6$ alkyl group, a substituted or unsubstituted branched $C_3$-$C_6$ alkyl group, or a substituted or unsubstituted $C_5$-$C_8$ cycloalkyl group, and wherein a substituted alkyl, alkenyl, alkynyl, cycloalkyl, or hydrocarbon group comprises a substituent selected from the group consisting of $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, amidino, guanidine, ureido, cyano, nitro, nitroso, azido, acyl, carbamate, thioacyl, acyloxy, carboxyl, and carboxylic ester.

2. The polymer of claim 1, wherein component (a) is at least one diamine of Structure (Ia).

3. The polymer of claim 2, wherein the amino group on the indane ring in Structure (Ia) is at the 5 position and the other amino group in Structure (Ia) is at the 4 position.

4. The polymer of claim 3, wherein each of $R^1$, $R^2$, and $R^3$ is CH$_3$ and each of $R^4$ and $R^5$ is H.

5. The polymer of claim 1, wherein each of $z^3$ and $z^4$ is 0.

6. The polymer of claim 5, wherein $R^{15}$ is a hydrogen atom or an unsubstituted linear $C_1$-$C_4$ alkyl.

7. The polymer of claim 1, wherein the diamine of Structure (IIa) is

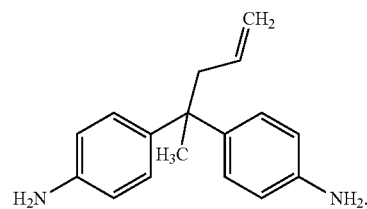

8. The polymer of claim 1, wherein the tetracarboxylic acid dianhydride is selected from the group consisting of:

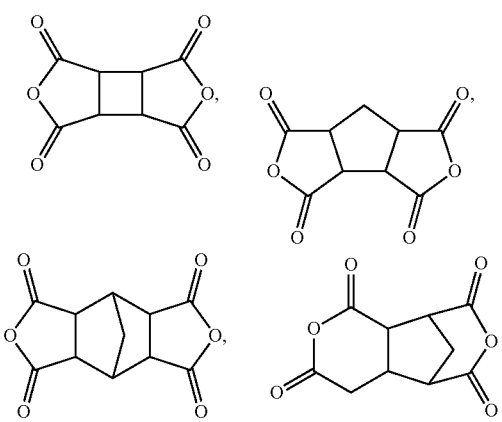

-continued

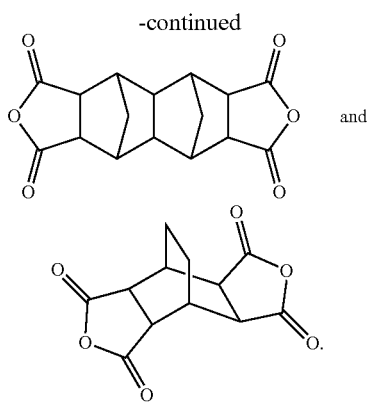
and

9. The polymer of claim 1, wherein the molar ratio of components (a) and (b) to component (c) ranges from 1.01 and 1.4.

10. The polymer of claim 1, wherein the molar ratio of components (a) and (b) to component (c) ranges from 0.8 and 0.99.

11. A polyamic acid polymer, comprising the reaction product of components (a), (b), (c), and optionally (d), wherein components (a), (b), (c), and (d) are:
(a) at least one diamine selected from the group consisting of a diamine of Structure (Ia) and a diamine of Structure (Ib):

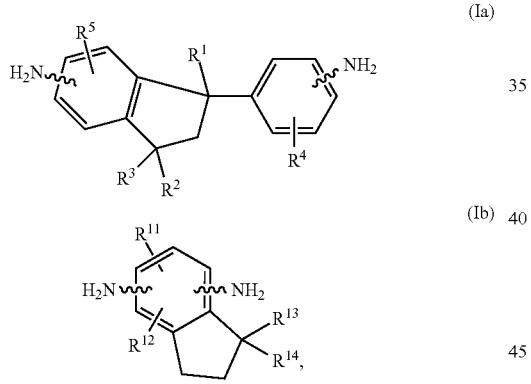

(b) at least one diamine of Structure (IIa):

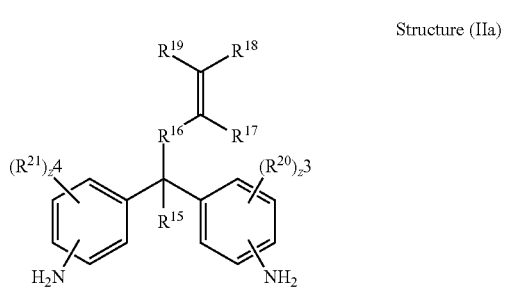

wherein
each of $z^3$ and $z^4$, independently, is an integer ranging from 0 to 4;
$R^{15}$ is a hydrogen atom, a substituted or unsubstituted linear or branched $C_1$-$C_4$ alkyl group, a substituted or unsubstituted branched $C_3$-$C_4$ alkyl group, a substituted or unsubstituted $C_5$-$C_8$ cycloalkyl group, a substituted or unsubstituted phenyl group, or —$R^{22}$—$C(R^{23})$=$C(R^{24}R^{25})$, in which $R^{22}$ is —$(CH_2)_z^6$—; each of $R^{23}$, $R^{24}$ and $R^{25}$, independently, is a hydrogen atom, a substituted or unsubstituted linear $C_1$-$C_4$ alkyl group, a substituted or unsubstituted branched $C_3$-$C_4$ alkyl group, a substituted or unsubstituted $C_5$-$C_8$ cycloalkyl group, or a substituted or unsubstituted phenyl group; and $z^6$ is an integer from 0 to 4;

$R^{16}$ is —$(CH_2)_z^5$—, in which $z^5$ is an integer from 1 to 4;

each of $R^{17}$, $R^{18}$, and $R^{19}$, independently, is a hydrogen atom, a substituted or unsubstituted linear $C_1$-$C_4$ alkyl group, a substituted or unsubstituted branched $C_3$-$C_4$ alkyl group, a substituted or unsubstituted $C_5$-$C_8$ cycloalkyl group, a substituted or unsubstituted phenyl group; and each $R^{20}$ and each $R^{21}$, independently, is a hydrogen atom, a substituted or unsubstituted linear $C_1$-$C_4$ alkyl group, a substituted or unsubstituted branched $C_3$-$C_4$ alkyl group, a substituted or unsubstituted $C_5$-$C_8$ cycloalkyl group or a halogen atom, (c) at least one tetracarboxylic acid dianhydride, and optionally, (d) at least one compound containing a first functional group reactive with an amine or an anhydride and at least one second functional group selected from the group consisting of a substituted or unsubstituted alkenyl group and a substituted or unsubstituted alkynyl group, wherein the first functional group reactive to an amine is selected from the group consisting of an anhydride group, an acid halide group, an epoxy group, and an isocyanate group and the first functional group reactive to an anhydride is selected from the group consisting of an amino group, a hydroxyl group, and a thiol group, wherein each of $R^1$, $R^2$, $R^3$, $R^4$, $R^5$, $R^{11}$, $R^{12}$, $R^{13}$, and $R^{14}$, independently, is H, a substituted or unsubstituted linear $C_1$-$C_6$ alkyl group, a substituted or unsubstituted branched $C_3$-$C_6$ alkyl group, or a substituted or unsubstituted $C_5$-$C_8$ cycloalkyl group, and wherein a substituted alkyl, alkenyl, alkynyl, cycloalkyl, or hydrocarbon group comprises a substituent selected from the group consisting of $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, amidino, guanidine, ureido, cyano, nitro, nitroso, azido, acyl, carbamate, thioacyl, acyloxy, carboxyl, and carboxylic ester.

12. The polyamic acid polymer of claim 11, wherein each of $z^3$ and $z^4$ is 0.

13. The polyamic acid polymer of claim 12, wherein $R^{15}$ is a hydrogen atom or an unsubstituted linear $C_1$-$C_4$ alkyl.

14. The polyamic acid polymer of claim 11, wherein the diamine of Structure (IIa) is

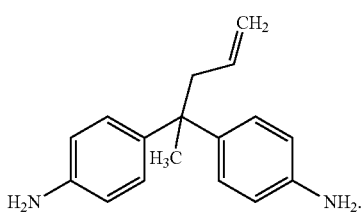 [SMILES: C=CCC(C)(c1ccc(N)cc1)c1ccc(N)cc1]

15. The polyamic acid polymer of claim 11, wherein the tetracarboxylic acid dianhydride is selected from the group consisting of:

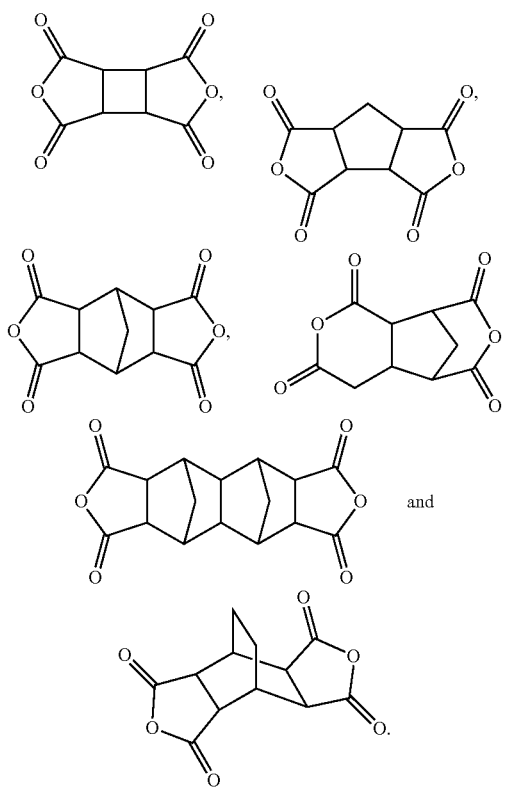

16. A composition, comprising:
(A) at least one polyimide polymer of claim 1;
(B) at least one reactive functional compound (RFC) having at least one functional group capable of reacting with a substituted or unsubstituted alkenyl group or a substituted or unsubstituted alkynyl group on the polyimide polymer, wherein the at least one functional group comprises a vinyl group, an allyl group, a vinyl ether group, a propenyl ether group, a (meth)acryloyl group, an epoxy group, a SiH group, or a thiol group;
(C) an initiator capable of initiating a reaction between a substituted or unsubstituted alkenyl group or a substituted or unsubstituted alkynyl group on the polyimide polymer and the RFC; and
(D) at least one solvent.

17. A process, comprising coating a substrate with the composition of claim 16 to form a coated substrate having a film on the substrate, and baking the coated substrate to form a coated substrate having a dried film.

18. The process of claim 17, wherein the coated substrate is baked at a temperature from about 50° C. to about 200° C.

19. The process of claim 18, further comprising exposing the dried film to radiation through a mask to form a coated substrate having a dried, patternwise exposed film.

20. The process of claim 19, further comprising baking the dried, patternwise exposed film at a temperature from about 50° C. to about 150° C. in a second baking step.

21. The process of claim 20, further comprising developing a portion of the dried, exposed film in a developer to produce a relief image on the substrate.

22. The process of claim 21, further comprising rinsing the relief image on the substrate with a solvent or a mixture of solvents.

23. The process of claim 22, further comprising baking the substrate having a relief image at a temperature from about 50° C. to about 200° C. in a third baking step.

24. An article formed by the process of claim 17, wherein the article is a semiconductor substrate, a flexible film for electronics, a wire isolation, a wire coating, a wire enamel, or an inked substrate.

25. A semiconductor device, comprising the article of claim 24.

26. The semiconductor device of claim 25, wherein the semiconductor device is an integrated circuit, a light emitting diode, a solar cell, and a transistor.

27. A dry film structure, comprising a carrier substrate, a protective layer, and a polymeric layer between the carrier substrate and the protective layer, wherein the polymeric layer contains:
(A) at least one polyimide polymer of claim 1;
(B) at least one reactive functional compound (RFC) having at least one functional group capable of reacting with a substituted or unsubstituted alkenyl group or a substituted or unsubstituted alkynyl group on the polyimide polymer; and
(C) an initiator capable of initiating a reaction between a substituted or unsubstituted alkenyl group or a substituted or unsubstituted alkynyl group on the polyimide polymer and the RFC.

28. A process, comprising:
(a) removing the protective layer from the dry film structure of claim 27;
(b) applying the structure obtained in step (a) onto an electronic substrate to form a laminate.

29. The process of claim 28, further comprising exposing the polymeric layer in the laminate to actinic radiation.

30. The process of claim 29, further comprising removing the carrier substrate before or after exposing the polymeric layer.

31. The process of claim 30, further comprising removing unexposed portions in the polymeric layer by using a developer.

32. The process of claim 31, further comprising curing the remaining polymeric layer.

33. An article formed by the process of claim 28, wherein the article is a semiconductor substrate, a flexible film for electronics, a wire isolation, a wire coating, a wire enamel, or an inked substrate.

34. An electronic device, comprising the article of claim 33.

35. The electronic device of claim 34, wherein the electronic device is an integrated circuit, a light emitting diode, a solar cell, or a transistor.

36. A polyimide polymer, comprising the reaction product of components (a), (b), (c), and optionally (d), wherein components (a), (b), (c), and (d) are:

(a) at least one diamine selected from the group consisting of a diamine of Structure (Ia) and a diamine of Structure (Ib):

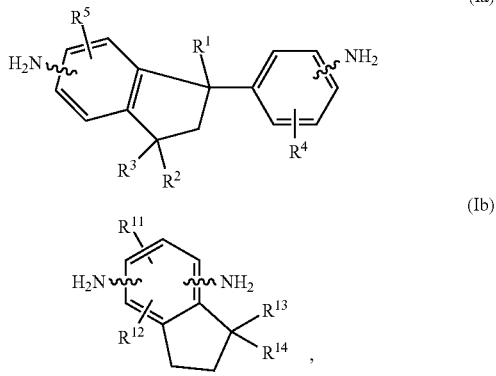
(Ia)

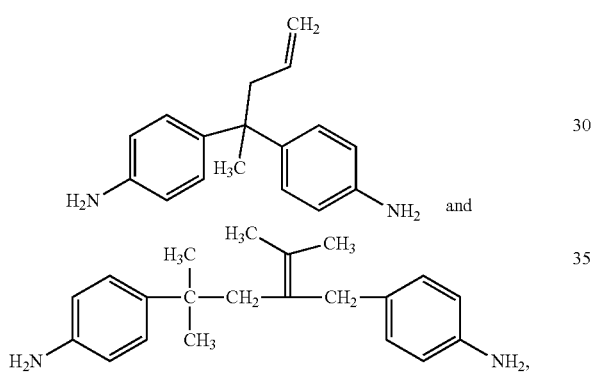
(Ib)

(b) at least one diamine selected from the group consisting of:

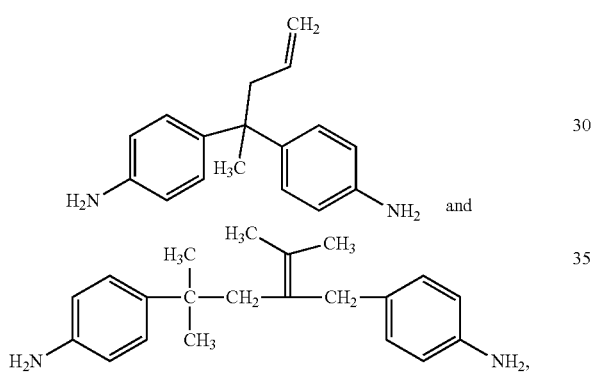

and (c) at least one tetracarboxylic acid dianhydride, and optionally (d) at least one compound containing a first functional group reactive with an amine or an anhydride and at least one second functional group selected from the group consisting of a substituted or unsubstituted alkenyl group and a substituted or unsubstituted alkynyl group, wherein the first functional group reactive to an amine is selected from the group consisting of an anhydride group, an acid halide group, an epoxy group, and an isocyanate group and the first functional group reactive to an anhydride is selected from the group consisting of an amino group, a hydroxyl group, and a thiol group, wherein each of $R^1$, $R^2$, $R^3$, $R^4$, $R^5$, $R^{11}$, $R^{12}$, $R^{13}$, and $R^{14}$, independently, is H, a substituted or unsubstituted linear $C_1$-$C_6$ alkyl group, a substituted or unsubstituted branched $C_3$-$C_6$ alkyl group, or a substituted or unsubstituted $C_5$-$C_8$ cycloalkyl group, and wherein a substituted alkyl, alkenyl, alkynyl, or cycloalkyl group comprises a substituent selected from the group consisting of $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, amidino, guanidine, ureido, cyano, nitro, nitroso, azido, acyl, carbamate, thioacyl, acyloxy, carboxyl, and carboxylic ester.

37. A polyamic acid polymer, comprising the reaction product of components (a), (b), (c), and optionally (d), wherein components (a), (b), (c), and (d) are:

(a) at least one diamine selected from the group consisting of a diamine of Structure (Ia) and a diamine of Structure (Ib):

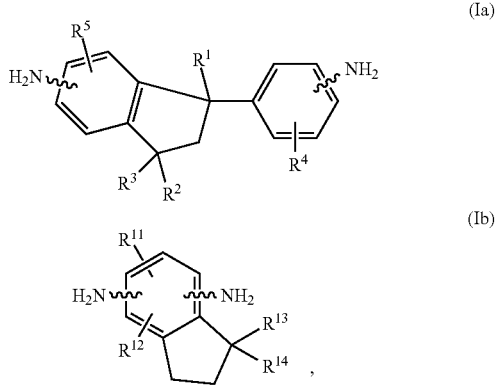
(Ia)

(Ib)

(b) at least one diamine selected from the group consisting of:

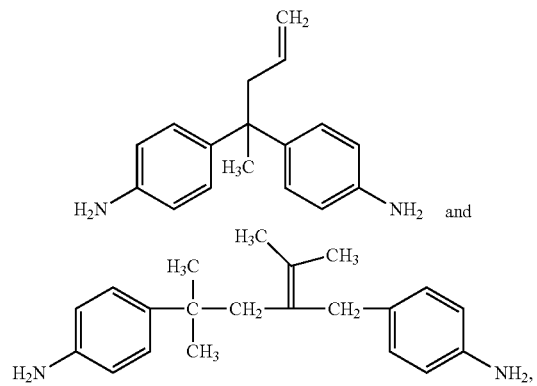

and (c) at least one tetracarboxylic acid dianhydride, and optionally (d) at least one compound containing a first functional group reactive with an amine or an anhydride and at least one second functional group selected from the group consisting of a substituted or unsubstituted alkenyl group and a substituted or unsubstituted alkynyl group, wherein the first functional group reactive to an amine is selected from the group consisting of an anhydride group, an acid halide group, an epoxy group, and an isocyanate group and the first functional group reactive to an anhydride is selected from the group consisting of an amino group, a hydroxyl group, and a thiol group, wherein each of $R^1$, $R^2$, $R^3$, $R^4$, $R^5$, $R^{11}$, $R^{12}$, $R^{13}$, and $R^{14}$, independently, is H, a substituted or unsubstituted $C_1$-$C_6$ linear $C_1$-$C_6$ alkyl group, a substituted or unsubstituted branched $C_3$-$C_6$ alkyl group, or a substituted or unsubstituted $C_5$-$C_8$ cycloalkyl group, and wherein a substituted alkyl, alkenyl, alkynyl, or cycloalkyl group comprises a substituent selected from the group consisting of $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, amidino, guanidine, ureido, cyano, nitro, nitroso, azido, acyl, carbamate, thioacyl, acyloxy, carboxyl, and carboxylic ester.

\* \* \* \* \*